(12) United States Patent
Åslund et al.

(10) Patent No.: US 7,820,645 B2
(45) Date of Patent: Oct. 26, 2010

(54) CRYSTALLINE FORMS

(75) Inventors: Bengt Leonard Åslund, Södertalje (SE); Stefan Bengtsson, Södertalje (SE); Gudrun Anita Bergman, Södertalje (SE); Ursula Renata Maria Hohlneicher, Mölndal (SE); Bo Ingvar Ymén, Södertalje (SE)

(73) Assignee: AstraZeneca AB, Sodertalje (SE)

( * ) Notice: Subject to any disclaimer, the term of this patent is extended or adjusted under 35 U.S.C. 154(b) by 43 days.

(21) Appl. No.: 11/950,568

(22) Filed: Dec. 5, 2007

(65) Prior Publication Data

US 2008/0287413 A1 Nov. 20, 2008

Related U.S. Application Data

(60) Provisional application No. 60/868,752, filed on Dec. 6, 2006.

(51) Int. Cl.
*A61K 31/397* (2006.01)
*A61P 43/00* (2006.01)
*C07D 205/04* (2006.01)

(52) U.S. Cl. .................. 514/210.17; 548/953
(58) Field of Classification Search ............ 514/210.17; 548/953
See application file for complete search history.

(56) References Cited

U.S. PATENT DOCUMENTS

| | | | |
|---|---|---|---|
| 4,346,078 A | 8/1982 | Bajusz et al. |
| 4,792,452 A | 12/1988 | Howard et al. |
| 5,053,416 A | 10/1991 | Toja et al. |
| 5,498,724 A | 3/1996 | Nystrom et al. |
| 5,559,232 A | 9/1996 | Ackermann et al. |
| 5,602,253 A | 2/1997 | Antonsson et al. |
| 5,659,071 A | 8/1997 | Nystrom et al. |
| 5,705,487 A | 1/1998 | Schacht et al. |
| 5,707,966 A | 1/1998 | Schacht et al. |
| 5,710,130 A | 1/1998 | Schacht et al. |
| 5,723,444 A | 3/1998 | Antonsson et al. |
| 5,744,487 A | 4/1998 | Ohshima et al. |
| 5,780,631 A | 7/1998 | Antonsson et al. |
| 5,783,563 A | 7/1998 | Antonsson et al. |
| 5,856,307 A | 1/1999 | Antonsson et al. |
| 5,939,392 A | 8/1999 | Antonsson et al. |
| 5,965,692 A | 10/1999 | Gustafsson et al. |
| 6,030,972 A | 2/2000 | Bohm et al. |
| 6,034,104 A | 3/2000 | Klimkowski et al. |
| 6,051,568 A | 4/2000 | Gustafsson et al. |
| 6,083,532 A | 7/2000 | Zhang et al. |
| 6,221,898 B1 | 4/2001 | Antonsson |
| 6,225,287 B1 | 5/2001 | Edvardsson et al. |
| 6,255,301 B1 | 7/2001 | Gustafsson et al. |
| 6,262,028 B1 | 7/2001 | Antonsson et al. |
| 6,265,397 B1 | 7/2001 | Karlsson et al. |
| 6,287,599 B1 | 9/2001 | Burnside et al. |
| 6,337,343 B1 | 1/2002 | Gustafsson et al. |
| 6,337,394 B2 | 1/2002 | Karlsson et al. |
| 6,433,186 B1 | 8/2002 | Inghardt et al. |
| 6,440,937 B1 | 8/2002 | Baucke et al. |
| 6,440,939 B2 | 8/2002 | Edvardsson et al. |
| 6,444,817 B1 | 9/2002 | Bohm et al. |
| 6,455,671 B1 | 9/2002 | Bohm et al. |
| 6,479,078 B1 | 11/2002 | Hedstrom et al. |
| 6,521,253 B1 | 2/2003 | Forsman et al. |
| 6,576,245 B1 | 6/2003 | Lundgren et al. |
| 6,576,657 B2 | 6/2003 | Karlsson et al. |
| 6,599,894 B1 | 7/2003 | Inghardt et al. |
| 6,617,320 B2 | 9/2003 | Gustafsson et al. |
| 6,660,279 B2 | 12/2003 | Lundgren et al. |
| 6,716,834 B2 | 4/2004 | Andersson et al. |
| 6,750,243 B1 | 6/2004 | Inghardt et al. |
| 6,811,794 B2 | 11/2004 | Burnside et al. |
| 6,838,478 B2 | 1/2005 | Gustafsson et al. |
| 6,875,446 B2 | 4/2005 | Forsman et al. |
| 6,888,007 B2 | 5/2005 | Edvardsson et al. |
| 6,921,758 B2 | 7/2005 | Gustafsson et al. |
| 6,984,627 B1 | 1/2006 | Antonsson et al. |
| 6,998,136 B2 | 2/2006 | Lundgren et al. |
| 7,056,907 B2 | 6/2006 | Inghardt et al. |
| 7,129,233 B2 | 10/2006 | Inghardt et al. |
| 7,202,236 B2 | 4/2007 | Magnusson et al. |
| 7,273,858 B2 | 9/2007 | Ahlqvist et al. |
| 2004/0019033 A1 | 1/2004 | Inghardt et al. |
| 2004/0242492 A1 | 12/2004 | Inghardt et al. |
| 2004/0242536 A1 | 12/2004 | Khoo et al. |
| 2005/0171083 A1 | 8/2005 | Magnusson et al. |

(Continued)

FOREIGN PATENT DOCUMENTS

EP 0185390 10/1991

(Continued)

OTHER PUBLICATIONS

Vippagunta et al., Advanced Drug Reviews, 48 (2001), pp. 3-26.*
Gupta et al. "Controlled-release tablets from carrageenans: effect of formulation, storage and dissolution factors" Eur. J. Pharm. Biopharm., 51(3):241-248 (2001).
Talukdar et al. "Comparative study on xanthan gum and hydroxypropylmethyl cellulose as matrices for controlled-release drug delivery I. Compaction and in vitro drug release behaviour" International Journal of Pharmaceutics, 129(2):233-241 (1996).
Baveja et al. "Zero-order release hydrophilic matrix tablets of beta-adrenergic blockers" International Journal of Pharmaceutics 39:39-45 (1987).

(Continued)

*Primary Examiner*—Yong Chu
(74) *Attorney, Agent, or Firm*—Morgan, Lewis & Bockius LLP

(57) ABSTRACT

There are provided crystalline forms of the compounds Ph(3-Cl)(5-OCHF$_2$)—(R)CH(OH)C(O)-Aze-Pab(OMe) and Ph(3-Cl)(5-OCHF$_2$)—(R)CH(OH)C(O)-Aze-Pab(OH), pharmaceutical compositions containing them, processes for obtaining them and their use in medical treatment.

5 Claims, 4 Drawing Sheets

U.S. PATENT DOCUMENTS

| | | |
|---|---|---|
| 2006/0014734 A1 | 1/2006 | Alami et al. |
| 2007/0202174 A1 | 8/2007 | Inghardt et al. |
| 2007/0218136 A1 | 9/2007 | Inghardt et al. |
| 2008/0050437 A1 | 2/2008 | Magnusson et al. |
| 2008/0090800 A1 | 4/2008 | Inghardt et al. |
| 2008/0269176 A1 | 10/2008 | Ahlqvist et al. |
| 2008/0293965 A1 | 11/2008 | Bosson |
| 2008/0312457 A1 | 12/2008 | Blixt et al. |
| 2008/0319206 A1 | 12/2008 | Al-Saffar et al. |

FOREIGN PATENT DOCUMENTS

| | | |
|---|---|---|
| EP | 0526877 | 2/1993 |
| EP | 0293881 | 3/1993 |
| EP | 0530167 | 3/1993 |
| EP | 0539059 | 4/1993 |
| EP | 0195212 | 11/1993 |
| EP | 0468231 | 9/1994 |
| EP | 0641779 | 3/1995 |
| EP | 0648780 | 4/1995 |
| EP | 0362002 | 7/1995 |
| EP | 0686642 | 12/1995 |
| EP | 0364344 | 5/1998 |
| EP | 0542525 | 7/1998 |
| EP | 0559046 | 7/2001 |
| EP | 0669317 | 9/2002 |
| EP | 0773955 | 4/2003 |
| EP | 0672658 | 9/2003 |
| JP | 57149217 | 9/1982 |
| WO | WO 93/11152 | 6/1993 |
| WO | WO 93/18060 | 9/1993 |
| WO | WO 94/29269 | 12/1994 |
| WO | WO 94/29336 | 12/1994 |
| WO | WO 95/23609 | 9/1995 |
| WO | WO 95/35309 | 12/1995 |
| WO | WO 96/03374 | 2/1996 |
| WO | WO 96/25426 | 8/1996 |
| WO | WO 96/26717 | 9/1996 |
| WO | WO 96/31504 | 10/1996 |
| WO | WO 96/32110 | 10/1996 |
| WO | WO 97/02284 | 1/1997 |
| WO | WO 97/23499 | 7/1997 |
| WO | WO 97/39770 | 10/1997 |
| WO | WO 97/46577 | 12/1997 |
| WO | WO 97/49404 | 12/1997 |
| WO | WO 98/01422 | 1/1998 |
| WO | WO 98/06740 | 2/1998 |
| WO | WO 98/16252 | 4/1998 |
| WO | WO 98/57932 | 12/1998 |
| WO | WO 99/21586 | 5/1999 |
| WO | WO 99/27913 | 6/1999 |
| WO | WO 99/29305 | 6/1999 |
| WO | WO 99/29664 | 6/1999 |
| WO | WO 99/39698 | 8/1999 |
| WO | WO 00/12043 | 3/2000 |
| WO | WO 00/13671 | 3/2000 |
| WO | WO 00/13710 | 3/2000 |
| WO | WO 00/14110 | 3/2000 |
| WO | WO 00/18352 | 4/2000 |
| WO | WO 00/35869 | 6/2000 |
| WO | WO 00/42059 | 7/2000 |
| WO | WO 01/02426 | 1/2001 |
| WO | WO 01/87879 | 11/2001 |
| WO | WO 02/14270 | 2/2002 |
| WO | WO 02/19990 | 3/2002 |
| WO | WO 02/44145 | 6/2002 |
| WO | WO 03/000293 | 1/2003 |
| WO | WO 03/018551 | 3/2003 |
| WO | WO 03/101957 | 5/2003 |
| WO | WO 03/090723 | 11/2003 |
| WO | WO 03/101423 | 12/2003 |
| WO | WO 03/101424 | 12/2003 |
| WO | WO 2005/054168 | 6/2005 |
| WO | WO 2006/090153 | 8/2006 |
| WO | WO 2006/125964 | 11/2006 |
| WO | WO 2008/068475 | 6/2008 |

OTHER PUBLICATIONS

Berge et al. "Pharmaceutical Salts" J. of Pharmaceutical Sciences 66(1): 1-19 (1977).

Bonferoni et al. "On the employment of lambda-carrageenan in a matrix system. II. Lambda-Carrageenan and hydroxypropyl-methylcellulose mixtures" J. Controlled Release 30:175-182 (1994).

CAS RN 159776-70-2 Dec. 1994.

CAS RN 192939-72-3 Aug. 1997.

CAS RN 30318-53-4 Nov. 2000.

Ham-Yong Park et al. "Effect of pH on Drug Release From Polysaccharide Tablets" Drug Delivery 5:13-18 (1998).

Picker "The use of carrageenan in mixture with microcrystalline cellulose and its functionality for making tablets" European J Pharmaceutics and Biopharmaceutics 48(1):27-36 (1999).

Talukdar et al. "In vivo evaluation of xanthan gum as a potential excipient for oral controlled-release matrix tablet formulation" International Journal of Pharmaceutics 169(1):105-113 (1998).

* cited by examiner

Release profile for Example 26

CRYSTALLINE FORMS

This application claims the benefit under 35 U.S.C. §119(e) of U.S. Application No. 60/868,752 filed on 6 Dec. 2006.

FIELD OF THE INVENTION

This invention relates to new solid state forms of certain drug compounds, to pharmaceutical compositions containing them, to processes for obtaining them and the use of the new solid state forms and compositions containing them in medical treatment.

BACKGROUND OF THE INVENTION

In the formulation of drug compositions, it is important for the drug substance to be in a form in which it can be conveniently handled and processed. This is of importance, not only from the point of view of obtaining a commercially viable manufacturing process, but also from the point of view of subsequent manufacture of pharmaceutical formulations (e.g. oral dosage forms such as tablets) comprising the active compound.

Further, in the manufacture of oral drug compositions, it is important that a reliable and reproducible plasma concentration profile of drug is provided following administration to a patient. This is of particular importance in the manufacture of compositions comprising anti-thrombotic agents.

Chemical stability, solid state stability and "shelf life" of the active ingredients are also very important factors. The drug substance, and compositions containing it, should be capable of being effectively stored over appreciable periods of time, without exhibiting a significant change in the active component's physico-chemical characteristics (e.g. its chemical composition, density, hygroscopicity and solubility).

Moreover, it is also important to be able to provide drug in a form which is as chemically pure as possible.

Amorphous materials may present problems in this regard. For example, such materials are typically difficult to handle and to formulate, provide for unreliable solubility, and are often found to be unstable and chemically impure.

The skilled person will appreciate that, if a drug can be readily obtained in a stable crystalline form, the above problems may be solved.

Thus, in the manufacture of commercially viable, and pharmaceutically acceptable, drug compositions, it is important, wherever possible, to provide drug in a substantially crystalline, and stable, form.

It is to be noted, however, that this goal is not always achievable. Indeed, typically, it is not possible to predict, from molecular structure alone, what the crystallisation behaviour of a compound, either as such or in the form of a salt, will be. This can only be determined empirically.

International patent application WO 02/44145 discloses a number of compounds, which have been found to be useful as thrombin inhibitors or prodrugs of thrombin inhibitors, which thrombin inhibitors are of the general formula I

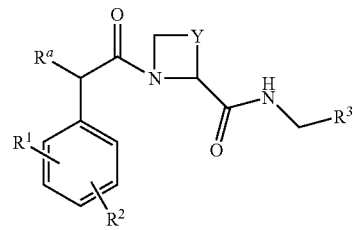

(wherein $R^a$, $R^1$, $R^2$, Y and $R^3$ have meanings given in the description of WO 02/44145) and pharmaceutically-acceptable derivatives (including prodrugs) thereof.

WO 02/44145 also specifically discloses the compounds Ph(3-Cl)(5-OCHF$_2$)—(R)CH(OH)C(O)-Aze-Pab(OMe), (referred to hereinafter as Compound A), wherein Aze represents (S)-azetidine-2-carboxylate and Pab represents para-amidinobenzylamino and Ph(3-Cl)(5-OCHF$_2$)—(R)CH(OH)C(O)-Aze-Pab(OH) (referred to hereinafter as Compound B).

Compound A

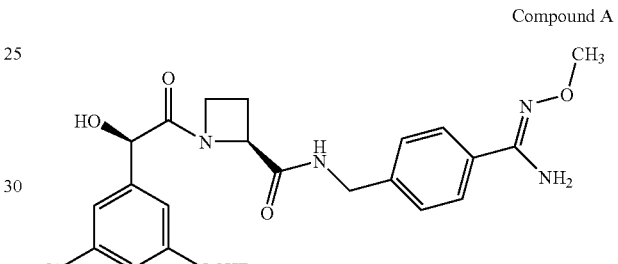

Compound B

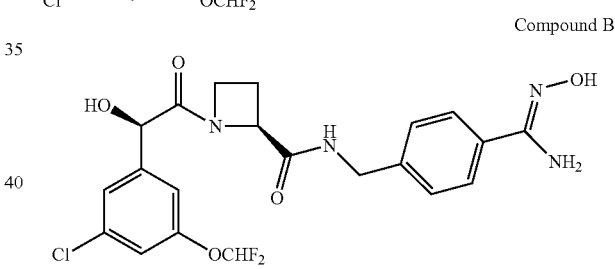

A process for the synthesis of Compounds A and B is described in the Examples of WO 02/44145, but Ph(3-Cl)(5-OCHF$_2$)—(R)CH(OH)C(O)-Aze-Pab(OMe) and Ph(3-Cl)(5-OCHF$_2$)—(R)CH(OH)C(O)-Aze-Pab(OH) in crystalline form are not disclosed.

Compounds A and B are metabolised following oral and/or parenteral administration to the corresponding free amidine compound (Compound C), which has been found to be an inhibitor of thrombin (see WO 02/44145, the relevant disclosure in which is hereby incorporated by reference).

Compound C

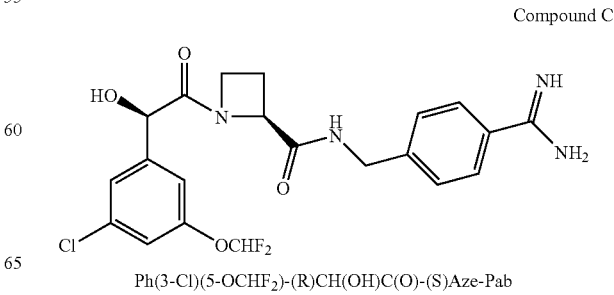

Ph(3-Cl)(5-OCHF$_2$)-(R)CH(OH)C(O)-(S)Aze-Pab

International patent application WO 03/101957 provides crystalline pharmaceutically-acceptable acid addition salts, such as ethanesulfonic acid, n-propanesulfonic acid, n-butane sulfonic acid and benzenesulfonic acid salts, of compounds such as Compound A.

However, there remains a need to find crystalline forms of such active compounds which are not in the form of salts. Such free-base crystalline forms allow formulations to be prepared without the requirement for a counter ion (which, for example, contributes "non-therapeutic" weight to the final formulation). For example, using the free base of compound A instead of the benzenesulfonic acid salt allows approximately a 30% decrease in weight, with a corresponding smaller tablet size.

DISCLOSURE OF THE INVENTION

We have now found that Ph(3-Cl)(5-OCHF$_2$)—(R)CH(OH)C(O)-Aze-Pab(OMe) and Ph(3-Cl)(5-OCHF$_2$)—(R)CH(OH)C(O)-Aze-Pab(OH) can be obtained in one or more non-salt forms that are substantially crystalline in nature.

Thus, according to a first aspect of the invention there are provided the compounds Ph(3-Cl)(5-OCHF$_2$)—(R)CH(OH)C(O)-Aze-Pab(OMe) and Ph(3-Cl)(5-OCHF$_2$)—(R)CH(OH)C(O)-Aze-Pab(OH) in substantially crystalline, non-salt forms (hereinafter referred to as "the compounds of the invention" or "solid state or crystalline forms of the invention").

Although we have found that it is possible to produce Ph(3-Cl)(5-OCHF$_2$)—(R)CH(OH)C(O)-Aze-Pab(OMe) and Ph(3-Cl)(5-OCHF$_2$)—(R)CH(OH)C(O)-Aze-Pab(OH) in forms which are greater than 80% crystalline, by "substantially crystalline" we include greater than 10% (e.g. greater that 20%), particularly greater then 30%, and more particularly greater than 40% crystalline. The degree (%) of crystallinity may be determined by the skilled person using X-ray powder diffraction (XRPD). Other techniques, such as solid state NMR, FT-IR, Raman spectroscopy, differential scanning calorimetry (DSC) and microcalorimetry, may also be used.

The compounds of the invention may be in a non-solvated form (such as an anhydrate) or in the form of a solvate, and all such forms are included as part of the invention. Solvates of Compound A or B include alcoholates such as an iso-propanol solvate (such as a compound of the invention which is in the form of an isopropanol solvate containing ⅓ isopropanol molecule per molecule of the compound of invention).

Additionally, any tautomers of the compounds of the invention are also included as part of the invention.

The compounds of the invention can have improved properties, for example stability, for example when compared with Ph(3-Cl)(5-OCHF$_2$)—(R)CH(OH)C(O)-Aze-Pab(OMe) and Ph(3-Cl)(5-OCHF$_2$)—(R)CH(OH)C(O)-Aze-Pab(OH) prepared as described in WO 02/44145. The compounds of the invention have different properties compared with their amorphous free-base forms and/or crystalline salt forms. For example, a different solubility and/or dissolution rate (in various solvents, for example aqueous systems) may be useful in formulations comprising the compounds of the invention (such as, for example, the crystalline form of Ph(3-Cl)(5-OCHF$_2$)—(R)CH(OH)C(O)-Aze-Pab(OMe) described herein).

According to a further aspect of the invention, there is thus provided a stable crystalline form of Ph(3-Cl)(5-OCHF$_2$)—(R)CH(OH)C(O)-Aze-Pab(OMe) and a stable crystalline form of Ph(3-Cl)(5-OCHF$_2$)—(R)CH(OH)C(O)-Aze-Pab(OH).

The term "stability" as defined herein includes chemical stability and/or solid state stability.

By "chemical stability", we include that the respective compounds can be stored in an isolated form, or in the form of a formulation in which it is provided in admixture with pharmaceutically acceptable carriers, diluents or adjuvants (e.g. in an oral dosage form, such as tablet, capsule etc.), under normal storage conditions, with a limited degree of chemical degradation or decomposition.

By "solid state stability", we include that the respective compounds can be stored in an isolated solid form, or in the form of a solid formulation in which it is provided in admixture with pharmaceutically acceptable carriers, diluents or adjuvants (e.g. in an oral dosage form, such as tablet, capsule etc.), under normal storage conditions, with an insignificant degree of solid state transformation (e.g. crystallisation, recrystallisation, solid state phase transition, hydration, dehydration, salvation or desolvation).

Examples of "normal storage conditions" include temperatures of between minus 80° C. and plus 50° C. (particularly between 0° C. and 40° C. and more particularly room temperatures, such as 15° C. to 30° C.), pressures of between 0.1 and 2 bars (particularly at atmospheric pressure), relative humidities of between 5 and 95% (particularly 10 to 75%), and/or exposure to 460 lux of UV/visible light, for prolonged periods (i.e. greater than or equal to six months). Under such conditions, compounds of the invention may be found to be less than 15%, more particularly less than 10%, and especially less than 5%, chemically degraded/decomposed, or solid state transformed, as appropriate. The skilled person will appreciate that the above-mentioned upper and lower limits for temperature, pressure and relative humidity represent extremes of normal storage conditions, and that certain combinations of these extremes will not be experienced during normal storage (e.g. a temperature of 50° C. and a pressure of 0.1 bar).

The compounds of the invention may be obtained advantageously by crystallising Ph(3-Cl)(5-OCHF$_2$)—(R)CH(OH)C(O)-Aze-Pab(OMe) or Ph(3-Cl)(5-OCHF$_2$)—(R)CH(OH)C(O)-Aze-Pab(OH) as described herein.

According to a further aspect of the invention, there is provided a process for the production of a compound of the invention which comprises crystallising Ph(3-Cl)(5-OCHF$_2$)—(R)CH(OH)C(O)-Aze-Pab(OMe) or Ph(3-Cl)(5-OCHF$_2$)—(R)CH(OH)C(O)-Aze-Pab(OH) from a supersaturated solution of the respective compound with a suitable solvent. In such a process it is important to leave the supersaturated solution mixed for a sufficient period of time. The length of time depends on the supersaturation so that highly supersaturated solutions may crystallise within a day or two, whereas less supersaturated solutions may require longer (for example a week or more).

In an environment free of seed-crystals it has been found that evaporation of solvent does not lead to crystallisation, so it is important to maintain a constant level of supersaturation (for example, by using a closed vessel).

Suitable mixing, for example by stirring, is believed to be important, possibly since it creates sites for primary, as well as secondary nucleation, thus speeding up the crystallisation process. Once available, the addition of seed crystals (of the form to be crystallised) to the supersaturated solution will speed up the crystallisation process since the time for primary nucleation will then be shortened. Thus, a further process of the invention provides the production of a compound of the invention which comprises crystallising Ph(3-Cl)(5-OCHF$_2$)—(R)CH(OH)C(O)-Aze-Pab(OMe) or Ph(3-Cl)(5-OCHF$_2$)—(R)CH(OH)C(O)-Aze-Pab(OH) from a (supersaturated) solution or slurry of the compound with a suitable solvent using seeds of the relevant compound to initiate and/or facilitate crystallisation. Suitable solvents include alcohols (such as ethanol and iso-propanol), ethyl acetate, isopropyl acetate, aqueous systems and suitable mixtures thereof (for example, water/ethanol, iso-propanol/ethyl acetate and iso-propyl acetate/ethanol/heptane). Anti-solvents may also be used as appropriate. A particular process of the invention comprises use of a three solvent system that favours aggregation of crystals, i.e use of a good solvent, a moderate solvent and an antisolvent, such as the good solvent ethanol, the moderate solvent isopropyl acetate and the antisolvent heptane.

In this way the crystallization time can be decreased from several days to about a day to reach a yield of about 90%. An increased amount of seed crystals (e.g. up to 4% w/w) and the timing of the antisolvent addition can decrease the crystallization time by such crystal nucleation.

According to the invention, crystalline Compound A or B can be obtained via crystallisation from a supersaturated solution of the respective amorphous compound in a suitable solvent. The supersaturated solution may be obtained following dissolution of the compound in a suitable solvent and evaporation to give the (amorphous) compound in question, followed by preparation of a suitable supersaturated solution. More advantageously, the supersaturated solution may be obtained from solutions which have been extracted directly from reaction solutions in which the compound in question has been formed; or, particularly advantageously, directly from reaction solutions within which the compound in question has been formed.

Further information on the processes of the invention and the products obtainable therefrom are described in the Examples herein.

Crystalline anhydrate material may be prepared as described herein by crystallising Compound A or B from one or more suitable solvents or mixtures thereof. Anhydrate may be produced by crystallisation from a solvent system which is substantially free of water (which may have been dried, and/or may be dried during the crystallisation process). However, crystalline anhydrate material (e.g. of Compound A) may also be prepared from water or water/ethanol mixtures.

Compounds of the invention that are anhydrates typically contain no more than 2%, particularly 1%, more particularly 0.5% and more particularly 0.2% (w/w) water, whether such water is bound (crystal water or otherwise) or not.

The crystalline isopropanol solvate may be prepared as described herein by crystallising (for example, Compound B) from a solvent system comprising isopropanol, or a combination of isopropanol and one or more other suitable solvents.

Compounds of the invention may be isolated using techniques which are well known to those skilled in the art, for example decanting, filtering or centrifuging.

Compounds of the invention may be dried using standard techniques. It will be appreciated by the skilled person that drying temperature and drying time may affect the solid state properties of compounds that are in the form of solvates (e.g. desolvation may occur at elevated temperatures and/or reduced pressure).

When compounds of the invention are crystallised, or recrystallised, as described herein, the resultant compound is in a form which has the improved chemical and/or solid state stability mentioned herein.

The crystalline forms of the compounds of the invention may be readily characterised using X-ray powder diffraction (XRPD) methods, for example as described hereinafter. Standard DSC and TGA techniques may also be used.

Pharmaceutical Preparations and Medical Uses

In accordance with the invention, the crystalline forms of the invention may be administered orally, intravenously, subcutaneously, buccally, rectally, dermally, nasally, tracheally, bronchially, by any other parenteral route, or via inhalation, in the form of a pharmaceutical preparation comprising the compound of the invention in a pharmaceutically acceptable dosage form. However we prefer that the compound of the invention is a form which is suitable for oral administration.

Depending on the disorder, and the patient to be treated, as well as the route of administration, the crystalline forms of the invention may be administered at varying doses (see below).

The crystalline forms of the invention may be further processed before formulation into a suitable pharmaceutical formulation, for example they may be milled or ground into smaller particles.

According to a further aspect of the invention, there is provided a pharmaceutical formulation including a crystalline form of the invention in admixture with a pharmaceutically acceptable adjuvant, diluent or carrier.

The amount of crystalline compound of the invention which is employed in such a formulation will depend on the condition, and patient, to be treated, as well as the crystalline form(s) which is/are employed, but can be determined non-inventively.

According to a further aspect of the invention, there is provided a pharmaceutical formulation including a compound of the invention in an immediate release formulation as described in International patent application WO 03/101423, the relevant disclosure of which document is hereby incorporated by reference.

The term "immediate release" pharmaceutical formulation includes any formulation in which the rate of release of drug from the formulation and/or the absorption of drug, is neither appreciably, nor intentionally, retarded by galenic manipulations. In the present case, immediate release may be provided for by way of an appropriate pharmaceutically acceptable diluent or carrier, which diluent or carrier does not prolong, to an appreciable extent, the rate of drug release and/or absorption. Thus, the term excludes formulations which are adapted to provide for "modified", "controlled", "sustained", "prolonged", "extended" or "delayed" release of drug.

In this context, the term "release" includes the provision (or presentation) of drug from the formulation to the gastrointestinal tract, to body tissues and/or into systemic circulation. For gastrointestinal tract release (in a fasting state), the release is under pH conditions such as pH=1 to 3, especially at, or about, pH=1. In one aspect of the invention a formulation as described herein with Compound A or B in crystalline form (hereinafter "Compound A or B") releases drug under a range of pH conditions. In another aspect of the invention a formulation as described herein with Compound A or B (in crystalline form) releases drug under pH conditions such as pH=1 to 3, especially at, or about, pH=1. Thus, formulations of the invention may release at least 70% (particularly 80%) of active ingredient within 4 hours, such as within 3 hours, particularly 2 hours, more particularly within 1.5 hours, and especially within an hour (such as within 30 minutes), of administration, whether this be oral or parenteral.

The formulations of the invention may be formulated in accordance with a variety of known techniques, for example as described by M. E. Aulton in "*Pharmaceutics: The Science* of *Dosage Form Design*" (1988) (Churchill Livingstone), the relevant disclosures in which document are hereby incorporated by reference.

Formulations of the invention may be, or may be adapted in accordance with standard techniques to be, suitable for peroral administration, for example in the form of an immediate release tablet, an immediate release capsule or as a liquid dosage form, comprising active ingredient. These formulation types are well known to the skilled person and may be prepared in accordance with techniques known in the art.

Suitable diluents/carriers (which may also be termed "fillers") for use in peroral formulations of the invention, for example those in the form of immediate release tablets, include monobasic calcium phosphate, dibasic calcium phosphate (including dibasic calcium phosphate dihydrate and dibasic calcium phosphate anhydrate), tribasic calcium phosphate, lactose, microcrystalline cellulose, silicified microcrystalline cellulose, mannitol, sorbitol, starch (such as maize, potato or rice), glucose, calcium lactate, calcium carbonate and the like. Particular diluents/carriers include dibasic calcium phosphate and microcrystalline cellulose, which may be used alone or in combination with another diluent/carrier such as mannitol.

A formulation of the invention in the form of an immediate release tablet may comprise one or more excipients to improve the physical and/or chemical properties of the final composition, and/or to facilitate the process of manufacture. Such excipients are conventional in the formulation of immediate release formulations for peroral drug delivery, and include one or more of the following: one or more lubricants (such as magnesium stearate, stearic acid, calcium stearate, stearyl alcohol or, particularly, sodium stearyl fumarate); a glidant (such as talc or a colloidal silica); one or more binders (such as polyvinylpyrrolidone, microcrystalline cellulose, a polyethylene glycol (PEG), a polyethylene oxide, a hydroxypropylmethylcellulose (HPMC) of a low molecular weight, a methylcellulose (MC) of a low molecular weight, a hydroxypropylcellulose (HPC) of a low molecular weight, a hydroxyethylcellulose (HEC) of a low molecular weight, a starch (such as maize, potato or rice) or a sodium carboxymethyl cellulose of a low molecular weight; (particular binders are polyvinylpyrrolidone or a HPMC of a low molecular weight); one or more pH controlling agents (such as an organic acid (for example citric acid) or an alkali metal (for example sodium) salt thereof, an oxide of magnesium, an alkali or alkaline earth metal (for example sodium, calcium or potassium sulphate, metabisulphate, propionate or sorbate); one or more disintegrant (for example sodium starch glycollate, a crosslinked polyvinylpyrrolidone, a crosslinked sodium carboxymethyl cellulose, a starch (such as maize, potato or rice) or an alginate); a colourant, a flavouring, a tonicity-modifying agent, a coating agent or a preservative.

It will be appreciated that some of the above mentioned excipients which may be present in a final immediate release oral (for example tablet) formulation of the invention may have more than one of the above-stated functions.

In a further aspect of the invention a liquid formulation of the invention is adapted to be suitable for oral administration.

Suitable liquid formulations that are to be administered orally include those in which Compound A or B is presented together with an aqueous carrier, such as water. A formulation of the present invention comprising an aqueous carrier may further comprise one or more excipients, such as an antimicrobial preservative; a tonicity modifier (for example sodium chloride, mannitol or glucose); a pH adjusting agent (for example a common inorganic acid or base, including hydrochloric acid or sodium hydroxide); a pH controlling agents (that is, a buffer; for example tartaric acid, acetic acid or citric acid); a surfactant (for example Sodiun dodecyl sulphate (SDS) or Solutol™); a solubiliser which serves to help solubilise the active ingredient (for example ethanol, a polyethylene glycol or hydroxypropyl-β-cyclodextrin or polyvinyl chloride (PVP)); or an antioxidant.

Liquid oral formulations may be in the form of suspensions of active ingredient in association with an aqueous solvent or, more particularly aqueous solutions (that is, solutions of active compound including water as a solvent). In this context, the term "aqueous solution" includes formulations in which at least 99% of active ingredient is in solution at above 5° C. and atmospheric pressure, and the term "suspension" means that more than 1% of active ingredient is not in solution under such conditions. Typical dispersion agents for suspensions are hydroxypropyl methylcellulose, AOT (dioctylsulfosuccinate), PVP and SDS. Other alternatives may be possible.

In another aspect the present invention provides a liquid oral formulation comprising Compound A or B, water and at least one additional agent. The additional agents include:
  i. polyethylene glycol (PEG) and optionally also ethanol and/or tartaric acid and/or citric acid and/or hydrochloric acid; or
  ii. sodium chloride (which will be dissolved in the formulation), and optionally also ethanol; or
  iii. hydrochloric acid and/or sodium hydroxide to bring the pH to a suitable value (particularly in the range 3-8); or
  iv. DMA (dimethyl acetamide) and optionally also a medium chain triglyceride (such as miglyol); or
  v. a β-cyclodextrin (such as hydroxypropyl-β-cyclodextrin);
  vi. a tonicity modifier such as sodium chloride and/or mannitol.

In a further aspect the present invention provides an oral solution comprising a Compound A or B, water and at least one additional agents as recited in (i) to (vi) above.

In another aspect the invention provides an aqueous formulation of Compound A or B comprising a solubilising agent such as a polyethylene glycol, β-cyclodextrin (such as hydroxypropyl-β-cyclodextrin), sorbitol or ethanol.

In a further aspect the present invention provides an oral solution formulation comprising Compound A or B and ethanol. This formulation can further comprise a medium chain triglyceride (such as miglyol).

In a still further aspect the present invention provides an oral solution formulation comprising a compound of formula (I) and DMA. This formulation can further comprise a medium chain triglyceride (such as miglyol).

In a further aspect of the invention a formulation of the invention is adapted to be suitable for parenteral administration. The term "parenteral" includes any mode of administration that does not comprise peroral administration to the gastrointestinal tract and includes administration subcutaneously, intravenously, intraarterially, transdermally, intranasally, intrabuccally, intracutaneously, intramuscularly, intralipomateously, intraperitoneally, rectally, sublingually, topically, by inhalation, or by any other parenteral route.

Suitable formulations of the invention that are to be administered parenterally include those in which Compound A or B is presented together with an aqueous carrier, such as water.

A formulation of the present invention comprising an aqueous carrier may further comprise one or more excipients, such as an antimicrobial preservative; a tonicity modifier (for example sodium chloride, mannitol or glucose); a pH adjusting agent (for example a common inorganic acid or base, including hydrochloric acid or sodium hydroxide); a pH controlling agents (that is, a buffer; for example tartaric acid, acetic acid or citric acid); a surfactant (for example sodium dodecyl sulphate (SDS) or Solutol™); a solubiliser which serves to help solubilise the active ingredient (for example ethanol, a polyethylene glycol or hydroxypropyl-β-cyclodextrin or polyvinyl chloride (PVP)); or an antioxidant.

Parenteral formulations may be in the form of suspensions of active ingredient in association with an aqueous solvent or, more particularly aqueous solutions (that is, solutions of active compound including water as a solvent). In this context, the term "aqueous solution" includes formulations in which at least 99% of active ingredient is in solution at above 5° C. and atmospheric pressure, and the term "suspension" means that more than 1% of active ingredient is not in solution under such conditions. Typical dispersion agents for suspensions are hydroxypropyl methylcellulose, AOT, PVP and SDS, but other alternatives are possible.

The number of excipients employed in the peroral and parenteral formulations of the invention depends upon many factors, such as the nature and amount of active ingredient present, and the amount of diluent/carrier (aqueous solvent or otherwise) that is included.

In another aspect the present invention provides a parenteral formulation comprising a Compound A or B, water and at least one additional agents. The additional agents include:
  i. polyethylene glycol (PEG) and optionally also ethanol and/or tartaric acid and/or hydrochloric acid; or
  ii. sodium chloride (which will be dissolved in the formulation), and optionally also ethanol; or
  iii. hydrochloric acid and/or sodium hydroxide to bring the pH to a suitable value (particularly in the range 3.5-8); or
  iv. DMA (dimethyl acetamide) and optionally also a medium chain triglyceride (such as miglyol); or
  v. a β-cyclodextrin (such as hydroxypropyl-β-cyclodextrin);
  vi. a tonicity modifier such as sodium chloride and/or mannitol.

In a further aspect the present invention provides an injectable solution comprising a Compound A or B, water and at least one additional agents as recited in (i) to (vi) above.

In another aspect the invention provides an aqueous formulation of Compound A or B comprising a solubilising agent such as a polyethylene glycol, β-cyclodextrin (such as hydroxypropyl-β-cyclodextrin), sorbitol or ethanol.

In a further aspect the present invention provides a parenteral formulation comprising Compound A or B and ethanol. This formulation can further comprise a medium chain triglyceride (such as miglyol).

In a still further aspect the present invention provides a parenteral formulation comprising a compound of formula (I) and DMA. This formulation can further comprise a medium chain triglyceride (such as miglyol).

In a still further aspect the present invention provides a solid formulation comprising microcrystalline cellulose and polyvinyl pyrrolidone (PVP); or comprising microcrystalline cellulose and sodium starch glycollate.

Formulations of the invention, such as parenteral formulations, comprising salts may be prepared by addition of diluent/carrier to the appropriate pre-prepared salt.

Compositions including active ingredient may also be provided in solid form suitable for use in the preparation of a formulation of the invention (for example a solution, such as an aqueous solution, for example for parenteral administration) ex tempore. Such compositions may be in the form of a solid comprising active ingredient, optionally in the presence of one or more further excipients as hereinbefore defined and, optionally, up to 10% (w/w) of diluent and/or carrier as hereinbefore defined, which compositions are hereinafter referred to as "the solid compositions of the invention".

Solid compositions of the invention may be made by removal of diluent/carrier (for example solvent) from a formulation of the invention, or a concentrated formulation of the invention, which may for example be in the form of a solution, such as an aqueous solution.

In another aspect the present invention provides an orally administerable, immediate release formulation comprising Compound A or B, a carrier (such as microcrystalline cellulose), a disintegrant (such as sodium starch glycollate), a binder (such as polyvinyl pyrrolidone) and a lubricant (such as sodium stearyl fumarate). Such a formulation may also comprise an additional carrier (or filler) such as mannitol.

Formulations of the invention that are in the form of immediate release tablets may be prepared by bringing active ingredient into association with diluent/carrier using standard techniques, and using standard equipment, known to the skilled person, including wet or dry granulation, direct compression/compaction, drying, milling, mixing, tableting and coating, as well as combinations of these processes, for example as described hereinafter. In one aspect of the invention, acid addition salts of compounds of formula (I) in crystalline form are formulated in tablets.

There is thus provided a process for the formation of a solid composition suitable for use in the preparation of a formulation of the invention (for example a solution, such as an aqueous solution) ex tempore, which process comprises removal of diluent/carrier (for example solvent) from a formulation of the invention, or a concentrated formulation of the invention.

Solvent may be removed by way of a variety of techniques known to those skilled in the art, for example evaporation (under reduced pressure or otherwise), freeze-drying, or any solvent removal (drying) process that removes solvent (such as water) while maintaining the integrity of the active ingredient. An example of drying is freeze-drying.

Thus according to a further aspect of the invention there is provided a freeze-dried (lyophilised) solid composition of the invention.

In the preparation of solid compositions of the invention, the skilled person will appreciate that appropriate additional excipients may be added at a suitable stage prior to removal of diluent/carrier. For example, in the case of aqueous solutions, pH may be controlled and/or adjusted as hereinbefore described. Furthermore, an appropriate additional excipient may be added with a view to aiding the formation of a solid composition of the invention during the process of diluent/carrier removal (for example mannitol, sucrose, glucose, mannose or trehalose).

A solid composition of Compound A or B, thus includes a composition in which the solvent (for example water) content, other than a solvent of crystallization, is no more than 10%, such as less than 2% unbound solvent, such as water.

Formulations of the invention may be sterilised, for example by sterile filtration or autoclavation, and/or filled into primary packages, such as vials, cartridges and pre-filled syringes. Such processing steps may also take place prior to drying to form a solid composition of the invention.

Before administration, the dried solid composition may be reconstituted and/or diluted in, for instance, water, physiological saline, glucose solution or any other suitable solution.

The amount of diluent/carrier in an oral (for example immediate release tablet) formulation of the invention depends upon many factors, such as the nature and amount of the active ingredient that is employed and the nature, and amounts, of any other constituents (for example further excipients) that are present in the formulation, but is typically up to 40% (w/w), particularly up to 30%, more particularly up to 20%, and particularly up to 10% (w/w) of the final composition. The amount of additional excipients in such an oral formulation of the invention also depends upon factors, such as the nature and amount of the active ingredient that is employed, as well as the nature, and amounts, of any other constituents (for example diluents/carriers and/or other further excipients) that are present in the formulation, but, for lubricants and glidants is typically up to 5% (w/w), and for binders and disintegrants is typically up to 10% (w/w) of the final composition.

The formulations of the invention are administered to mammalian patients (including humans), and according to a further aspect of the invention there is thus provided a formulation of the invention for use as a pharmaceutical.

According to a further aspect of the invention, there is provided a pharmaceutical formulation including a compound of the invention in a modified release formulation as described in International patent application WO 03/101424, the relevant disclosure of which document is hereby incorporated by reference.

The term "modified release" pharmaceutical composition will be well understood by the skilled person to include any composition/formulation in which the onset and/or rate of release of drug is altered by galenic manipulations, and thus includes the definition provided in the *United States Pharmacopeia* (USP XXII) at pages xliii and xliv of the preface/preamble part, the relevant disclosure in which document is hereby incorporated by reference.

In the present case, modified release may be provided for by way of an appropriate pharmaceutically-acceptable carrier, and/or other means, which carrier or means (as appropriate) gives rise to an alteration of the onset and/or rate of release of active ingredient. Thus, the term will be understood by those skilled in the art to include compositions which are adapted (for example as described herein) to provide for a "sustained", a "prolonged" or an "extended" release of drug (in which drug is released at a sufficiently retarded rate to produce a therapeutic response over a required period of time, optionally including provision for an initial amount of drug being made available within a predetermined time following administration to cause an initial desired therapeutic response); compositions which provide for a "delayed" release of drug (in which the release of drug is delayed until a specific region of the gastrointestinal tract is reached, following which drug release may be either pulsatile or further modified as indicated above); as well as so-called "repeat action" compositions (in which one dose of drug is released either immediately or some time after administration and further doses are released at a later time).

We prefer that the compositions of the invention provide for a delayed release or, more particularly, a sustained (that is prolonged or extended) release of drug over a period of time. More particular compositions of the invention may be adapted (for example as described herein) to provide a sufficient dose of drug over the dosing interval (irrespective of the number of doses per unit time) to produce a desired therapeutic effect. Release may be uniform and/or constant over an extended period of time, or otherwise.

Compositions of the invention may, for example, be in the form of one or more the following, all of which are well known to those skilled in the art:

(a) Coated pellets, tablets or capsules, which may be designed to release at least some of the drug when the formulation in question reaches a particular region of the gastrointestinal tract. Such tablets may, for example be provided with some form of gastro-resistant coating, such as an enteric coating layer, providing for release of at least part of the drug present in the formulation in a specific part of the gastrointestinal tract, such as the intestinal regions.

(b) Multiple unit or multiparticulate systems, which may be in the form of microparticles, microspheres or pellets comprising drug (which multiple units/multiparticulates may provide for gradual emptying of the formulation containing drug from the stomach into the duodenum and further through the small and large intestine while releasing drug at a pre-determined rate).

(c) Formulations comprising dispersions or solid solutions of active compound in a matrix, which may be in the form of a wax, gum or fat, or, particularly, in the form of a polymer, in which drug release takes place by way of gradual surface erosion of the tablet and/or diffusion.

(d) Systems which comprise a bioadhesive layer, which layer may provide for prolonged retention of composition of the invention in a particular region of the gastrointestinal tract (for example the stomach). This includes floating or sinking systems (that is low and high density systems, respectively), as well as so-called "volume-enlarging" systems.

(e) So-called "pendent" devices, in which drug is attached to an ion exchange resin, which provides for gradual release of drug by way of influence of other ions present in the gastrointestinal tract, for example, the acid environment of the stomach.

(f) Devices in which release rate of drug is controlled by way of its chemical potential (for example the Osmotic Pump).

(g) Systems in which drug is released by diffusion through membranes, including multilayer systems.

(h) Devices that act in accordance with an external signal, to release a small amount of drug.

(i) Active, self-programmed systems, which may contain a sensing element, which element responds to a particular biological environment to modulate drug delivery.

(j) Silastic controlled release depots, which release drug as a function of diffusion of water and/or gastrointestinal fluids into the device via an entry/exit port, resulting in dissolution and subsequent release of drug.

The above principles are discussed at length in prior art references including *Pharmaceutisch Weekblad Scientific Edition*, 6, 57 (1984); *Medical Applications of Controlled Release*, Vol II, eds. Langer and Wise (1984) Bocaraton, Fla., at pages 1 to 34; *Industrial Aspects of Pharmaceuticals*, ed. Sandel, Swedish Pharmaceutical Press (1993) at pages 93 to 104; and pages 191 to 211 of *"Pharmaceutics: The Science of Dosage Form Design"*, ed. M. E. Aulton (1988) (Churchill Livingstone); as well as the references cited in the above-mentioned documents, the disclosures in all of which documents are hereby incorporated by reference.

In a further aspect the invention provides a modified release formulation which comprises a gelling matrix. The matrix particularly comprises hydroxy propyl methyl cellulose (HPMC), iota-carrageenan, sodium dodecyl sulphate (SDS) and/or xanthan gum. More particularly the matrix comprises hydroxy propyl methyl cellulose (HPMC), iota-carrageenan and/or PEO. The HPMC may be one or a mixture of two or more HPMCs of different viscosities or molecular weights (as described anywhere below).

The invention also provides a modified release formulation comprising one or more HPMCs and one or more further components selected from the group comprising: iota-carrageenan, microcrystalline cellulose, a lubricant (such as sodium stearyl fumarate) or mannitol.

The invention further provides, in a further aspect, a modified release formulation comprising xanthan gum; or comprising iota-carrageenan and PEO (as described below).

Suitable modified release formulations may thus be prepared in accordance with standard techniques in pharmacy, as described herein or in the above-mentioned documents, and/or which are well known.

In particular, in compositions of the invention, active ingredient is provided together with a pharmaceutically acceptable carrier. A particular composition of the invention is presented in the form of active ingredient in a polymer matrix.

In this respect, in particular the compositions of the invention are provided for oral administration in the form of a so-called "swelling" modified-release system, or a "gelling matrix" modified-release system, in which active ingredient is provided together with a polymer that swells in an aqueous medium (that is a "hydrophilic gelling component"). The term "aqueous medium" is to be understood in this context to include water, and liquids which are, or which approximate to, those present in the gastrointestinal tract of a mammal. Such polymer systems typically comprise hydrophilic macromolecular structures, which in a dry form may be in a glassy, or at least partially crystalline, state, and which swell when contacted with aqueous media.

Modified release of drug is thus effected by one or more of the following processes: transport of solvent into the polymer matrix, swelling of the polymer, diffusion of drug through the swollen polymer and/or erosion of the polymer, one or more of which may serve to release drug slowly from the polymer matrix into an aqueous medium.

Thus, suitable polymeric materials (acting as carriers), which may be used as the hydrophilic gelling component of a gelling matrix modified-release composition include those with a molecular weight of above 5000 g/mol, and which either:

(a) are at least sparingly soluble in; or
(b) swell when placed in contact with, aqueous media (as defined hereinbefore), so enabling release of drug from the carrier.

Suitable gelling matrix polymers, which may be synthetic or natural, thus include polysaccharides, such as maltodextrin, xanthan, scleroglucan dextran, starch, alginates, pullulan, hyaluronic acid, chitin, chitosan and the like; other natural polymers, such as proteins (albumin, gelatin etc.), poly-L-lysine; sodium poly(acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; poly(ethylene oxide) (PEO); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

For the compositions of the invention in the form of gelling matrix systems, we prefer that the principal swelling polymer that is employed is HPC, maltodextrin, scleroglucan or carboxypolymethylene, more particularly, PEO or xanthan, and, especially, HPMC, as well as copolymers and/or (simple) mixtures of any of these polymers. Iota-carrageenan is an alternative.

When PEO, xanthan and HPMC are employed in (that is, as at least one of the polymers of) the hydrophilic gelling component, preferred molecular weights (that is, weight average molecular weights, as determined by standard techniques, such as osmometry, size-exclusion chromatography with a refraction detector (in which molecular weight is determined by way of standard calibration curves), light scattering and/or ultracentrifuge techniques), for these polymers are in the range 5,000 g/mol up to 200,000,000 g/mol, such as up to 100,000,000 g/mol, particularly up to 25,000,000 g/mol and more particularly up to 20,000,000 g/mol. Mixtures of PEO, xanthan and HPMC polymers with different molecular weights within these ranges may be employed.

Suitable HPMC polymers also include those that produce 2% w/w solutions of polymer in water with viscosities, as measured by standard techniques, such as those described generally in the *United States Pharmacopeia* XXIV (USP XXIV/NF19) at page 2002 et seq, as well as, specifically, at pages 843 and 844 (the relevant disclosures in which document are hereby incorporated by reference), of between 3 and 150,000 cps (at 20° C.), such as between 10 and 120,000 cps, particularly between 30 and 50,000 cps and more particularly between 50 and 15,000 cps. Mixtures of HPMC polymers with different viscosities within these ranges may be employed, in order, for example, to produce HPMC mixtures which produce solutions as mentioned above with "average" viscosities (i.e. a viscosity for the mixture) within the above-mentioned preferred ranges. Similarly, mixtures of HPMC polymers (with viscosities and/or "average" viscosities within these ranges) with other above-mentioned polymers may be employed. Suitable HPMC polymers include those fulfilling the *United States Pharmacopeia* standard substitution types 2208, 2906, 2910 and 1828 (see USP XXIV/NF19 for further details). Suitable HPMC polymers thus include those sold under the trademark METHOCEL™ (Dow Chemical Corporation) or the trademark METOLOSE™ (Shin-Etsu).

Suitable xanthan polymers include those that produce 1% w/w solutions of polymer in water with viscosities, as measured by standard techniques, such as those described generally in the *United States Pharmacopeia* XXIV (USP XXIV/NF19) at page 2002 et seq, as well as, specifically, at pages 2537 and 2538 (the relevant disclosures in which document are hereby incorporated by reference), of between 60 and 2,000 cps (at 24° C.), for example between 600 and 1,800 cps and particularly between 1,200 and 1,600 cps. Mixtures of xanthan polymers with different viscosities within these ranges may be employed, in order, for example, to produce xanthan mixtures which produce solutions as mentioned above with "average" viscosities (i.e. a viscosity for the mixture) within the above-mentioned preferred ranges. Similarly, mixtures of xanthan polymers (with viscosities and/or "average" viscosities within these ranges) with other above-mentioned polymers may be employed. Suitable xanthan polymers include those sold under the trademarks XANTURAL™ and KELTROL™ (CPKelco), and SATIAXANE™ (Degussa, Texturant Systems).

The choice of polymer will be determined by the nature of the active ingredient/drug that is employed in the composition of the invention as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the invention in the form of gelling matrix systems in which the polymer carrier is provided by way of a blend of two or more polymers of, for example, different molecular weights, for example as described hereinafter, in order to produce a particular required or desired release profile.

When in the form of gelling matrix systems, we have also found that rate of release of drug from compositions of the invention may be further controlled by way of controlling the drug:polymer ratio within, and the surface area:volume ratio of, individual compositions (for example tablets) comprising drug and polymer carrier system.

Compositions of the invention, whether in the form of a gelling matrix system or otherwise, may contain one or more further excipients (in addition to the polymer carrier system) to further modify drug release, to improve the physical and/or chemical properties of the final composition, and/or to facilitate the process of manufacture. Such excipients are conventional in the formulation of modified release compositions.

For example, compositions of the invention may contain one or more of the following diluents: calcium phosphate (monocalcium phosphate, dicalcium phosphate and tricalcium phosphate), lactose, microcrystalline cellulose, mannitol, sorbitol, titanium dioxide, aluminium silicate and the like. Particular diluents include microcrystalline cellulose and also mannitol.

Compositions of the invention may contain one or more of the following lubricants: magnesium stearate, sodium stearyl fumarate and the like.

Compositions of the invention may contain a glidant, such as a colloidal silica.

Compositions of the invention may contain one or more of the following binders: polyvinylpyrrolidone, lactose, mannitol, microcrystalline cellulose, a polyethylene glycol (PEG), a HPMC of a low molecular weight, a MC of a low molecular weight, a HPC of a low molecular weight and the like. Particular binders include microcrystalline cellulose.

Compositions of the invention may contain one or more of the following pH controlling agents: organic acids (for example. citric acid and the like) or alkali metal (for example sodium) salts thereof, pharmaceutically acceptable salts (for example sodium, magnesium or calcium salts) of inorganic acids (such as carbonic acid or phosphoric acid), oxides of magnesium, as well as alkali, and alkaline earth metal (for example sodium, calcium, potassium and the like) sulphates, metabisulphates, propionates and sorbates.

Other further excipients may include colourants, flavourings, solubilising agents (such as SDS), coating agents, preservatives, etc.

Combinations of the above-stated further excipients may be employed.

It will be appreciated that some of the above mentioned further excipients, which may be present in the final composition of the invention, may have more than one of the above-stated functions. Moreover, further excipients mentioned above may also function as part of a hydrophilic gelling component in a gelling matrix system.

The total amount of further excipients (not including, in the case of gelling matrix systems, the principal polymer carrier(s)) that may be present in the composition of the invention will depend upon the nature of the composition, as well as the nature, and amounts of, the other constituents of that composition, and may be an amount of up to 85%, for example between 0.1 to 75%, such as 0.2 to 65%, particularly 0.3 to 55%, more particularly 0.5 to 45% and especially 1 to 40%, such as 2 to 35% w/w. In any event, the choice, and amount, of excipient(s) may be determined routinely (that is without recourse to inventive input) by the skilled person.

In gelling matrix systems, the amount of polymer in the system should be enough to ensure that a sufficient dose of drug is provided over the dosing interval to produce the desired therapeutic effect. Thus, for a gelling matrix system, we prefer that it takes at least 2 hours (particularly at least 4 hours, especially at least 6 hours) for 80% (especially 60%) of the initial drug content of the composition to be released to a patient after administration under the test conditions described hereinafter, and particularly over a period of between 8 and 24 hours. Most particularly at least 80% of the initial drug content of the composition is released at a time somewhere between 8 and 24 hours. Suitable amounts of polymer that may be included, which will depend upon inter alia the active ingredient that is employed in the composition, any excipients that may be present and the nature of the polymer that is employed, are in the range 5 to 99.5%, for example 10 to 95%, particularly 30 to 80% w/w. In any event, the choice, and amount, of polymer may be determined routinely by the skilled person.

In another particular formulation we prefer that the compounds of the invention are formulated together in a gelling matrix composition comprising iota-carrageenan and one or more neutral gelling polymers.

Iota-carrageenan is particularly present in such a particular preparation at a level of more that 15% by weight. Particular grades of iota-carrageenan include pharmaceutical grade iota-carrageenan (for example, available from FMC Biopolymer), which has a viscosity of not less than 5 centipoise (cps), particularly in the range 5-10 cps (for a 1.5% solution warmed to 82° C., after which the viscosity is measured at 75° C. with a Brookfield LV viscometer fitted with a #1 spindle running at a speed of 30 rpm), and technical grade iota-carrageenan (for example, available from Fluka Biochemica), which particularly has a viscosity of not less than 14 mPa·s, for a 0.3% aqueous solution warmed to 20° C., after which the viscosity is measured using a fallingball viscometer, of type Haake, used together with a Lauda thermostat C3 and Hakke Mess-System III, and using gold-coated stainless steel balls of density 7.8 g/cm$^3$.

The neutral gelling polymer may be a single, or a mixture of more than one, neutral polymer(s) having gelling properties and having substantially pH-independent solubility. The neutral gelling polymer is, particularly, present in the formulation at a level of more that 10% but particularly more than 20% by weight.

Suitable neutral gelling polymers include polyethylene oxide (PEO), derivatives and members of the PEO family (for example, polyethylene glycol (PEG)), particularly existing naturally in the solid state, of suitable molecular weight or viscosity. If used as a single neutral gelling polymer, a PEO particularly has a MW of $\geq$4 million (4 M), corresponding to an aqueous solution viscosity range of 1650-5500 mPa·s (or 1650-5500 cps; measured for a 1% aqueous solution at 25° C., using a Brookfield RVF viscometer, with No. 2 spindle, at 2 rpm). Other examples of suitable PEOs include a PEO of MW around 5 million (5 M), corresponding to an aqueous solution viscosity range of 5500-7500 mPa·s, or a PEO MW around 8 million (8 M), corresponding to an aqueous solution viscosity range of 10000-15000 mPa·s. This range covers the value for typical solution viscosity (in cps) measured at 25° C., quoted for this polymer, in the USP 24/NF 19, 2000 edition, pp. 2285-2286. If PEG is used as a single neutral gelling polymer it particularly has a high molecular weight, for example, a MW of around 20000, corresponding to a viscosity range of 2700-3500 mPa·s (or 2700-3500 cps), measured using a 50% aqueous solution (w/w) at 20° C., using a capillary viscometer (Ubbelohde or equivalent). [Ref: European Pharmacopoeia $3^{rd}$ Ed., 2000, Supplement, pp. 908-909.]

Other suitable neutral gelling polymers include cellulose derivatives such as hydroxypropylmethyl cellulose (HPMC) or hydroxyethylcellulose (HEC) with suitably high viscosities (for example "HPMC 50 cps", "HPMC 10000 cps", "HPMC 15000 cps", "HEC type HH" or "HEC type H"). When used as a single neutral polymer, hydroxypropylmethyl cellulose polymers like "HPMC 10000 cps" and "HPMC 15000 cps" have, respectively, apparent viscosities of 7500-14000 mPa·s (or 7500-14000 cps), and 11250-21000 mPa·s (or 11250-21000 cps), when measured at 20° C. with a 2% (w/w) aqueous solution, calculated with reference to the dried substance, using a capillary viscometer (Ubbelohde or equivalent). One type of hydroxyethylcellulose polymer, for example, "Natrosol 250 Pharma, type HH", from Hercules Incorporated (Aqualon), shows typically a Brookfield viscosity of about 20,000 mPa·s using a Brookfield Synchro-Lectric Model LVF instrument, at the conditions 1% solution concentration, spindle no. 4, spindle speed 30 rpm, factor 200, 25° C. (See Natrosol Physical and Chemical Properties booklet, 33.007-E6 (1993), p. 21).

Particular formulations that may be mentioned include those in which compound of the invention is formulated together with iota-carageenan and HPMC (10,000 cps) in a 50:50 (wt %) ratio, or together with iota-carageenan and HPMC (50 cps) & HPMC (10,000 cps) in a 35:60:5 (wt %) ratio, or together with iota-carageenan and PEO 4M in a 50:50 (wt %) ratio. Particular additional excipients in such formulations include lubricants, such as sodium stearyl fumarate.

In one aspect the invention provides a non-injectable formulation of the invention comprising Compound A or B; an HPMC and a lubricant (such as sodium stearyl fumarate). In a further aspect the formulation may comprise a mixture of 2 or more HPMCs of different viscosities (such as 10,000 cPs and 50 cPs). Further, the formulation may additionally comprise a solubilising agent [such as sodium dodecyl sulphate (SDS), sodium lauryl sulphate or polyoxyl 40 hydrogenated castor oil].

Suitable amounts of active ingredient in the compositions of the invention, whether in the form of gelling matrix systems or otherwise, depend upon many factors, such as the nature of that ingredient (free base/salt etc), the dose that is required, and the nature, and amounts, of other constituents of the composition. However, they may be in the range 0.5 to 80%, for example 1 to 75%, such as 3 to 70%, particularly 5 to 65%, more particularly 10 to 60% and especially 15 to 55% w/w. In any event, the amount of active ingredient to be included may be determined routinely by the skilled person.

A typical daily dose of Compound A or B is in the range 0.001 to 100 mg/kg body weight of free base, irrespective of the number of individual doses that are administered during the course of that day. A particular daily dose is in the range 20-600 mg.

Compositions of the invention such as those described hereinbefore may be made in accordance with well known techniques such as those described in the references mentioned hereinbefore. Compositions of the invention that are in the form of gelling matrix systems may be prepared by standard techniques, and using standard equipment, known to the skilled person, including wet or dry granulation, direct compression/compaction, drying, milling, mixing, tabletting and coating, as well as combinations of these processes, for example as described hereinafter.

Although compositions of the invention are particularly adapted to be administered orally, their use is not limited to that mode of administration. Parenteral modified release compositions of the invention, which may include systems that are well known to those skilled in the art, such as those based upon poloxamers, biodegradable microspheres, liposomes, suspensions in oils and/or emulsions, may be prepared in accordance with standard techniques, for example as described by Leung et al in "*Controlled Drug Delivery: Fundamentals and Applications*" (*Drugs and the Pharmaceutical Sciences*; vol. 29), $2^{nd}$ edition, eds. Robinson and Lee, Dekker (1987) at Chapter 10, page 433, the disclosure in which document is hereby incorporated by reference.

The compositions of the invention may be dosed once or more times daily (particularly once, but no more than twice, daily), irrespective of the number of individual units (formulations/compositions) that are administered as part of one "dose".

The formulations of the invention are administered to mammalian patients (including humans) and according to a further aspect of the invention there is thus provided a formulation of the invention for use as a pharmaceutical.

The compounds of the invention are useful because they are metabolised in the body following administration to form compounds which possess pharmacological activity. They are therefore indicated as pharmaceuticals, and in particular as prodrugs of pharmacologically-active compounds.

In particular, the compounds of the invention are metabolised in the body to form potent inhibitors of thrombin, for example as demonstrated in the tests described in WO 02/44145. The compounds of the invention are expected to be useful in the treatment of conditions where inhibition of thrombin is required or desirable, including those described in WO 02/44145, the disclosure in which document is hereby incorporated by reference. Example 46 of WO 02/44145 discloses that the compound of Example 3 of WO 02/44145 (i.e. Compound C disclosed herein) was tested in Test A of WO 02/44145 and found to exhibit $IC_{50}$ TT values of less than 0.02 μM. Example 47 of WO 02/44145 discloses that the compound of Example 3 of WO 02/44145 (i.e. Compound C disclosed herein) was tested in Test D of WO 02/44145 and found to exhibit an $IC_{50}$ APTT value of less than 1 μM. Compound C is formed by metabolism (in-vivo) of the compounds of the present invention.

Suitable doses of a compound of the invention in the therapeutic and/or prophylactic treatment of mammalian, especially human, patients are in the range 2 to 600 mg (particularly in the range 20 to 500 mg) per day at peroral administration, and 1 to 100 mg per day at parenteral administration and/or 0.003 to 60 mg/kg, particularly 0.03 to 15 mg/kg, body weight per day at peroral administration and 0.0015 to 30 mg/kg, particularly 0.015 to 7.5 mg/kg, body weight at parenteral administration.

According to a further aspect of the invention there is provided a method of treatment of a condition where inhibition of thrombin is required or desired, which method includes administering a therapeutically effective amount of a compound of the invention to a patient in need of such treatment. For the avoidance of doubt, by "treatment" we include the therapeutic treatment, as well as the prophylaxis, of a condition (such as cardiovascular disorders including venous thrombosis, pulmonary embolism, arterial thrombosis, systemic embolism and atrial fibrillation). Also provided is a method of administering compound C by administering a compound of the invention, and a method of using a compound of the invention to administer compound C.

Also provided is a compound of the invention for use as a pharmaceutical, in particular for use in treating a cardiovascular disorder such as venous thrombosis, pulmonary embolism, arterial thrombosis, systemic embolism or atrial fibrillation.

The compounds of the invention have the advantage that they are in a form which provides for improved ease of handling. Further, the compounds of the invention have the advantage that they may be produced in forms which have improved chemical and solid state stability (including lower hygroscopicity). Thus, the compounds may be stable when stored over prolonged periods.

Compounds of the invention may also have the advantage that they may be crystallised in good yields, in a higher purity, more conveniently and/or at a lower cost than forms of Ph(3-Cl)(5-OCHF$_2$)—(R)CH(OH)C(O)-Aze-Pab(OMe) or Ph(3-Cl)(5-OCHF$_2$)—(R)CH(OH)C(O)-Aze-Pab(OH) prepared previously.

According to a further aspect of the invention there is provided a compound obtainable by any of the processes or Examples described herein.

EXAMPLES

The invention is illustrated, but in no way limited, by the following Examples and with reference to the enclosed Figures.

The following abbreviations may be used:
Aze=(S)-azetidine-2-carboxylate (unless otherwise specified)
Boc=tert-butoxycarbonyl
CBA=para-cyano-benzylamine
Pab=para-amidinobenzylamino
EDC=1-(3-dimethylaminopropyl)-3-ethylcarbodiimide hydrochloride
TBTU=[N,N,N',N'-tetramethyl-O-(benzotriazol-1-yl)-uronium tetrafluoroborate]
SMB=simulated moving bed chromatography system General Procedures X-ray powder diffraction analysis (XRPD) was performed on samples prepared according to standard methods, for example those described in Giacovazzo, C. et al (1995), *Fundamentals of Crystallography*, Oxford University Press; Jenkins, R. and Snyder, R. L. (1996), *Introduction to X-Ray Powder Diffractometry*, John Wiley & Sons, New York; Bunn, C. W. (1948), *Chemical Crystallography*, Clarendon Press, London; or Klug, H. P. & Alexander, L. E. (1974), *X-ray Diffraction Procedures*, John Wiley and Sons, New York. X-ray analyses were performed using a Siemens D5000 diffractometer and/or a Philips X'Pert PRO. Some samples were also prepared by stirring the precipitation to create a slurry and then, using a Pasteur pipette, withdrawing approximately 0.2 ml of this and putting it on a Silicon Zero Background Holder. This slurry was then analysed in a standard way, both as wet and subsequently also when dried. Samples prepared in this way are more prone to "preferred orientation effects" than those prepared using a dry sample, by the standard methods.

Differential scanning calorimetry (DSC) was performed using a Mettler DSC820 or a Perkin Elmer DSC7 instrument, according to standard methods, for example those described in Höhne, G. W. H. et al (1996), *Differential Scanning Calorimetry*, Springer, Berlin.

Thermogravimetric analysis (TGA) was performed using a Mettler Toledo TGA850 or a Perkin Elmer TGA7 instrument.

Forms prepared in accordance with the Examples below showed "essentially" the same XRPD diffraction patterns and/or DSC and/or TGA thermograms as other Examples disclosed below, when it was clear from the relevant patterns/thermograms (allowing for experimental error) that the same crystalline form had been formed. Thus, DSC onset temperatures may vary in the range ±5° C. (e.g. ±2° C.), and XRPD distance values may vary in the range ±2 on the last decimal place. It should be noted that some XRPD samples exhibited such strong preferred orientation effects that the intensity of some peaks were completely attenuated whereas others were much enhanced. The diffractograms shown in the Figures are of the type showing less preferred orientation effects.

Preparation of Starting Materials

Amorphous Compound A and amorphous Compound B may be prepared as described, for example, according to the procedures described in WO 02/44145 (relevant sections of which are hereby incorporated by reference). Relevant starting materials and intermediates may be obtained, for example, as described in relevant sections of WO/054168 and WO 06/090153 (relevant sections of which are also hereby incorporated by reference).

Amorphous Compound A can be prepared according to the following general scheme 1 . . . .

Scheme 1

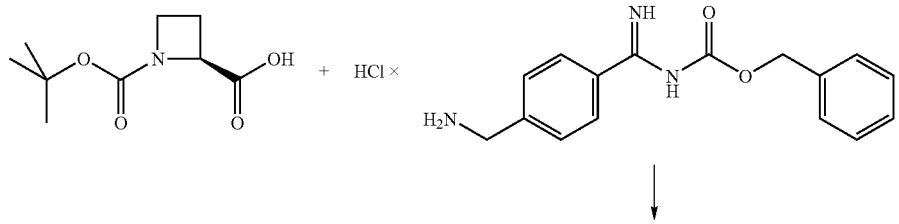

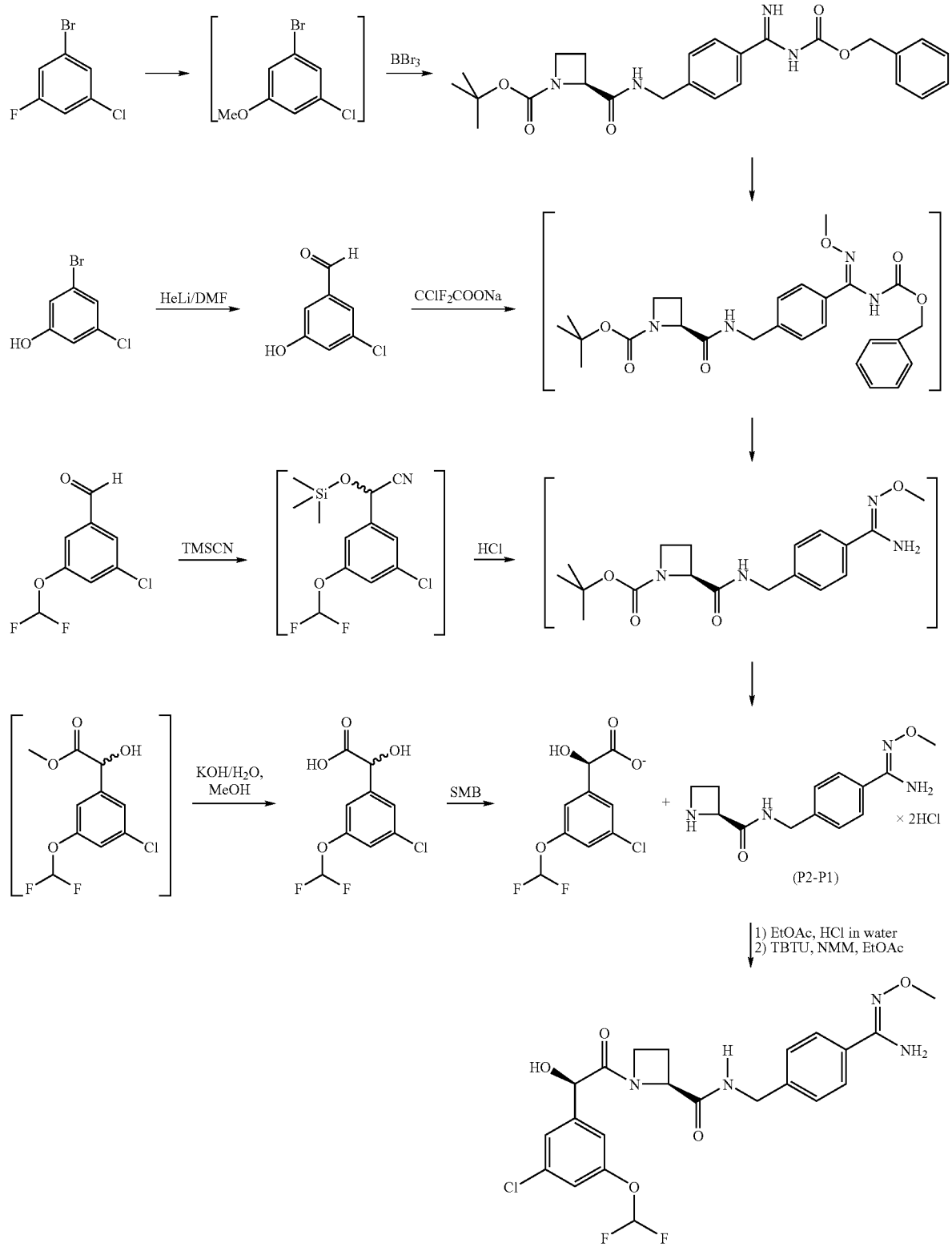

The final coupling was also performed in dichloromethane solvent at approximately 22° C. using DIPEA and TBTU (substituted mandelic acid: 1.08 kg (4.16 mol); (P2-P1): 1.40 kg (4.16 mol); dichloromethane: 16.5 L; DIPEA: 2.1 L (12.27 mol); TBTU: 1.37 kg (4.16 mol).). Work-up was by EtOAc addition (22 L), concentration in vacuo and extraction using water (17 L+17.5 L+EtOAc 16 L) and washing with half-saturated sodium carbonate solution (8.5 L). The crude material was purified by chromatography using a column packed with SiO$_2$ (conditioned with eluant-dichloromethane/methanol: 20/1) and eluted with the dichloromethane/methanol: 20/1 eluant. After concentration in vacuo of combined product fractions the residue was dissolved in methanol, filtered, concentrated and dried.

Amorphous Compound B can be prepared by coupling 3-chloro-5-difluoromethoxy mandelic acid (prolinamide salt—see structure below) to Aze-CBA.hydrochloride salt (which can be prepared by deprotecting Boc-Aze-CBA—see structure below).

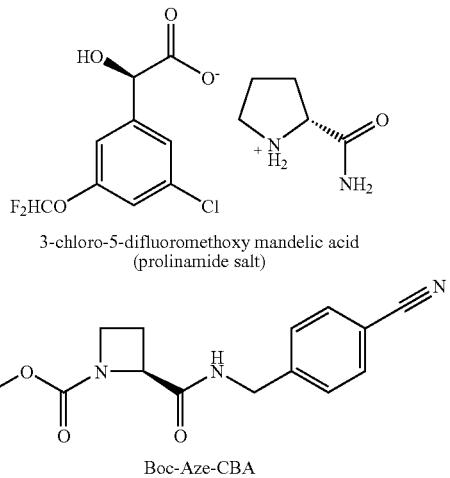

3-chloro-5-difluoromethoxy mandelic acid
(prolinamide salt)

Boc-Aze-CBA

The coupling has been performed as follows. . . .

3-Chloro-5-difluoromethoxy mandelic acid prolinamide salt (5.699 kg, 15.54 mol) was added to EtOAc (28.5 L) at below 7° C. and then HCl (3.6%, 28 L) added whilst keeping the temperature below 5° C. After stirring for 35 minutes, the layers were separated and the aqueous layer extracted using EtOAc (27 L). Both organic layers were combined, filtered over MgSO4 (2.1 kg) and washed with EtOAc (16 L). To the dried organic layer was added Aze-CBA.HCl (3.91 kg, 15.54 mol) at below 22° C.; DIPEA: 8 L (46.62 mol) and TBTU: 7.49 kg (23.31 mol) and the mixture stirred for approximately 17 hours at approximately 22° C.

The mixture was washed with water (2×29 L), 2×Na$_2$CO$_3$ (27 L+29.5 L), 2×HCl (3.6%; 29 L+28.6 L), 2×NaCl (12%; 28.2 L+28.5 L) then during extraction with NaCl (23.1%: 2 L). Washing was repeated with NaHCO$_3$ (7.4%; 2 L) and NaCl (12%; 28 L) then during extraction with NaCl (23.1%; 3 L). To the organic volume (37 L) was added EtOAc (18 L) and 20 L distilled off. Methylcyclohexane (35 L) was added, the mixture cooled to 3° C., filtered after approximately 16.5 hours and the filter cake washed with EtOAc/methyl cyclohexane (1/1; 6 L of each) to give 5.147 kg of solid product.

Amorphous Compound B can then be obtained by converting the cyano group of the 3-chloro-5-difluoromethoxy mandelic acid-Aze-CBA coupled product to the required hydroxyl-amidine function by use of NH$_2$OH.HCl and Hunig's base (or DIPEA or triethylamine) in ethanol (at a temperature below 2° C.).

In particular, this reaction has been performed as follows . . . .

Hydroxylamine hydrochloride (1.49 kg, 21.53 mol) was added to a mixture of the 3-chloro-5-difluoromethoxy mandelic acid-Aze-CBA coupled product (3.229 kg, 7.18 mol) in ethanol (21 L) at approximately 2° C. DIPEA (3.7 L, 21.62 mol) was added and the mixture stirred for approximately 46 hours at approximately 2° C. Work-up was by addition of acetone (1.32 L, 17.95 mol) at below 5° C. and EtOAc (61 L) and water (61 L). The separated organic layer was extracted with water (25 L) and NaCl solution (23.1%, 5 L) used during the extraction. Solvent (30 L) was distilled off and then EtOAc (11 L) added. More solvent was distilled off and MeOH (5 L) added. Final distillation yielded 3.378 kg of solid product.

The product was purified by mixing with iso-propanol, refluxing for approximately 4 hours, cooling and filtering. Finally, the solid was suspended in methanol and evaporated, followed by use of ethyl acetate solvent & evaporation.

SUMMARY OF FIGURES

Crystals obtained as described herein were analyzed by XRPD and the results are tabulated below (RI represents relative intensity) and are shown in the respective Figures.

Table 1 directly below shows the most significant peaks in the XRPD-diffractogram of crystalline anhydrate of Compound A.

A number of weak and very weak peaks have been omitted. RI-values in parenthesis show how the peak is affected by preferred orientation effects. Due to preferred orientation effects some of the weak omitted peaks may become more significant.

| d-value/Å | RI |
|---|---|
| 15.2 | m |
| 10.8 | m |
| 6.8 | m |
| 6.0 | m |
| 5.4 | w (vs) |
| 5.2 | s |
| 4.79 | s (vs) |
| 4.46 | w (vw) |
| 4.37 | m (vw) |
| 4.23 | s (m) |
| 3.98 | s (vs) |
| 3.79 | w |
| 3.62 | w (vw) |
| 3.57 | w (m) |
| 3.43 | m (vw) |
| 3.20 | m (w) |
| 3.10 | w |

Figure 2:
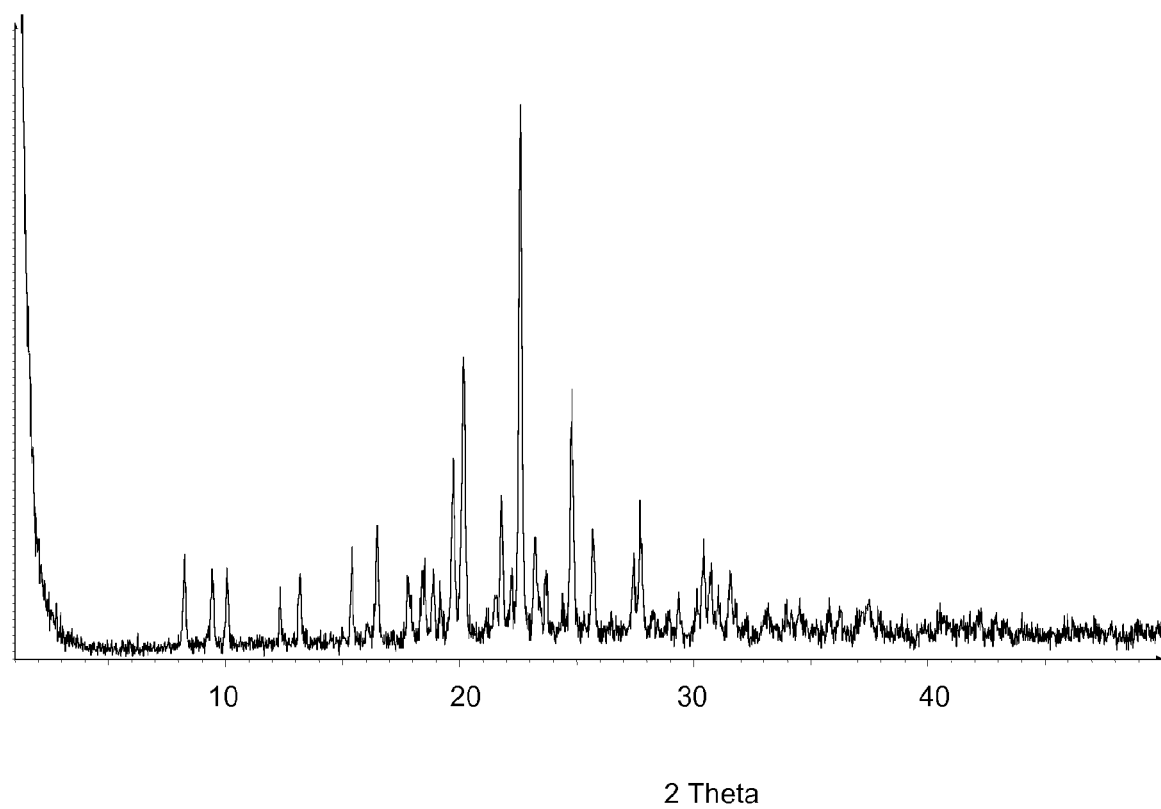

FIG. 2 shows the XRPD-diffractogram of crystalline anhydrate of Compound B.

Table 2 directly below shows the most significant peaks in the XRPD-diffractogram of crystalline anhydrate of Compound B.

A number of weak and very weak peaks have been omitted.

| d-value/Å | RI |
|---|---|
| 10.8 | w |
| 9.4 | w |
| 8.8 | w |
| 7.2 | w |
| 6.7 | w |
| 5.8 | w |
| 5.4 | m |

-continued

| d-value/Å | RI |
|---|---|
| 4.51 | m |
| 4.41 | s |
| 4.08 | m |
| 3.94 | vs |
| 3.83 | m |
| 3.59 | s |
| 3.47 | m |
| 3.22 | m |

Figure 3:
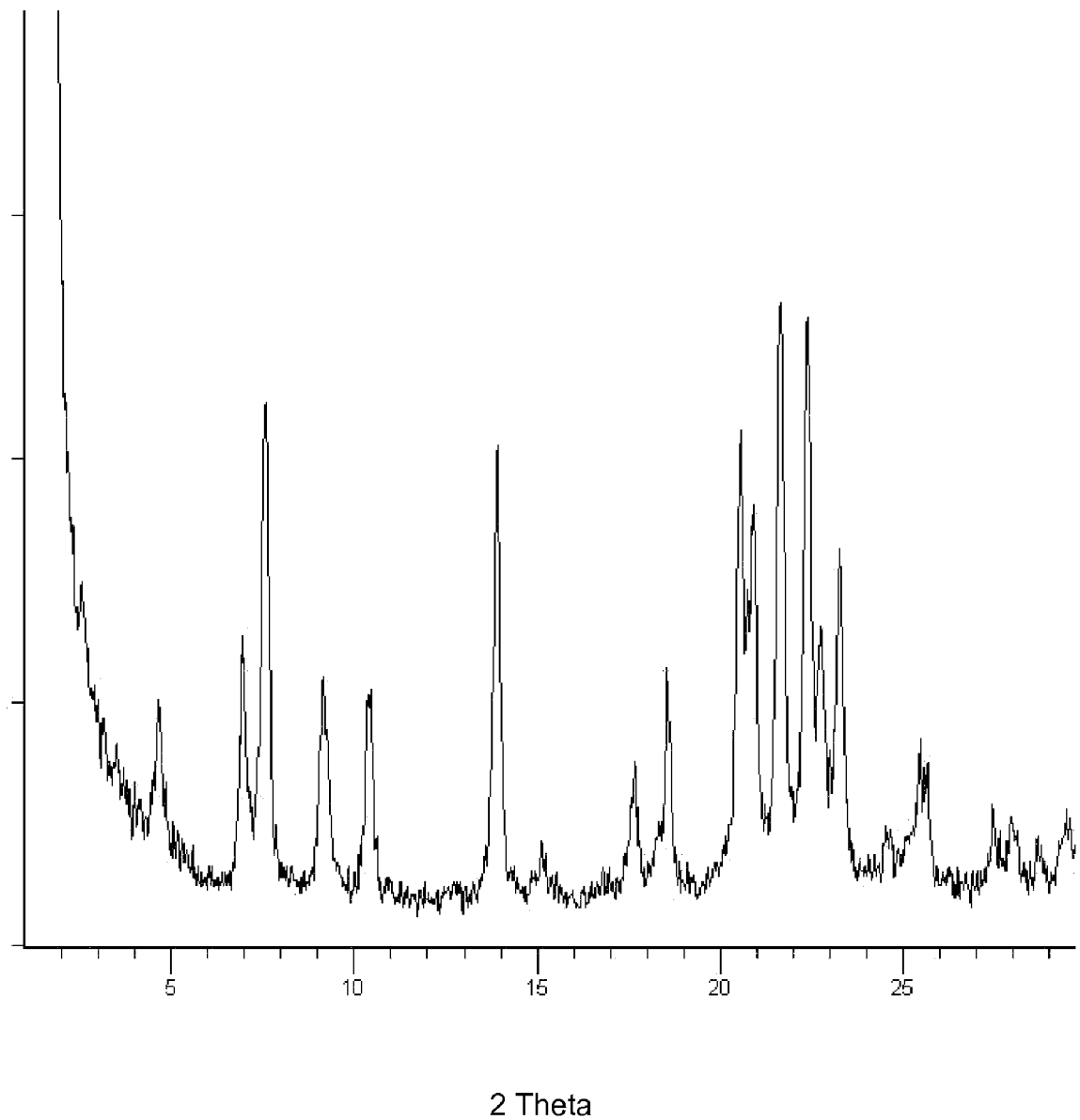

FIG. 3 shows the XRPD-diffractogram of crystalline ⅓-isopropanolate of Compound B.

Table 3 directly below shows the most significant peaks in the XRPD-diffractogram of crystalline isopropanolate of Compound B.

A number of weak and very weak peaks have been omitted.

| d-value/Å | RI |
|---|---|
| 18.9 | w |
| 12.7 | m |
| 11.7 | s |
| 9.6 | m |
| 8.5 | m |
| 6.4 | s |
| 5.0 | w |
| 4.78 | m |
| 4.28 | s (broad) |
| 4.10 | s |
| 3.97 | s |
| 3.91 | m |
| 3.82 | m |

Abbreviations
vs = very strong; s = strong; m = medium; w = weak; vw = very weak; broad = several peaks overlapping.

Particular aspects of the invention include (i) The compound Ph(3-Cl)(5-OCHF$_2$)—(R)CH(OH)C(O)-Aze-Pab(OMe) anhydrate in crystalline form with an X-ray powder diffraction pattern characterized by peaks with d-values at 5.2 Å, 4.79 Å, 4.23 Å and 3.98 Å.

(ii) The compound Ph(3-Cl)(5-OCHF$_2$)—(R)CH(OH)C(O)-Aze-Pab(OH). anhydrate in crystalline form with an X-ray powder diffraction pattern characterized by peaks with d-values at 4.41 Å, 3.94 Å and 3.59 Å.

(iii) The compound Ph(3-Cl)(5-OCHF$_2$)—(R)CH(OH)C(O)-Aze-Pab(OH).⅓ isopropanolate in crystalline form with an X-ray powder diffraction pattern characterized by peaks with d-values at 11.7 Å, 6.4 Å, 4.1 Å and 3.97 Å.

Figure 4:
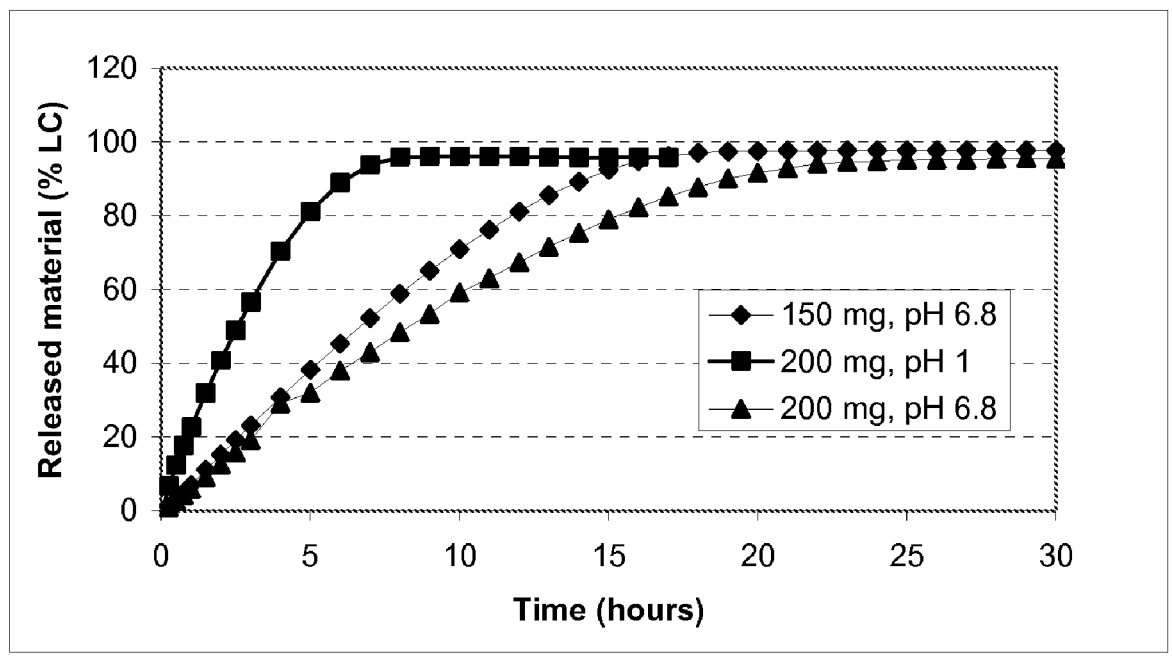

FIG. 4 shows the release profile of 150 mg and 200 mg gelling matrix formulations for Example 26.

EXAMPLE 1

Crystallisation of Compound B

Amorphous Compound B (31.21 mg) was added to a mixture of ethanol/water 20:80 w/w (3.06 g) and the sample was shaken for a couple of hours. As the solid was almost completely dissolved another 10 mg of amorphous Compound B was added and the resulting suspension was left shaking for 5 days. The saturated solution was then decanted off and the solid sample was put in a refrigerator for two hours before it was analysed with XRPD. The sample was now crystalline and the resulting diffractogram is shown in FIG. 2. Later the sample was analysed with TGA and DSC. The weight loss between 25-110° C. was 0.13% and the DSC thermogram had one endothermic peak at an onset temperature of 170° C. and an enthalpy of 106 J/g.

EXAMPLE 2

Crystallisation of Compound B

Amorphous Compound B was dissolved in isopropanol and stirred for 2 hours in a closed vessel. During this time crystallization had occurred. The sample was analysed with XRPD and polarized light microscopy and was found to be only partly crystalline. It was therefore left to slurry for two more days, also in a closed vessel. A sample was then withdrawn on a glass filter (porosity 4) and analysed with XRPD. It was now highly crystalline and the XRPD-diffractogram obtained is shown in FIG. 3. Analysis with DSC gave one endotherm with peak at 95° C., onset value at 82° C. and enthalpy of 127 J/g. TGA analysis gave a weight loss up to 105° C. of 8%. The sample was then dried for 2 days at 22° C. in vacuum and re-analysed. The DSC now gave an endothermic peak at 97° C. (onset value=84° C.) and an enthalpy of 112 J/g. The TGA weight loss below 105° C. was now 6.8%.

EXAMPLE 3

Crystallisation of Compound A 2.5 ml of isopropanol was mixed and stirred with amorphous Compound A (75 mg) in a closed vessel. After 17 hours it had crystallised. A small amount of isopropanol was added and stirred to form a slurry, which was then filtered on a glass filter porosity 4. The solid obtained was dried under vacuum at 22° C. and crystal formation was verified with polarized light microscopy (by visual inspection of crystals between crossed polarizers).

EXAMPLE 4

Crystallisation of Compound B

Amorphous Compound B (0.5 g) was mixed with ca. 5 ml isopropanol in a closed vessel. After a few hours a thick precipitate had formed. A couple of mL of isopropanol was added so that stirring was smoother. The precipitation was checked with polarized light microscopy and, as for Example 2 above, it was found that crystals were mixed with amorphous gel. The mixture was stirred over 2 days (also in a closed vessel) and then analysed with polarized light microscopy to show that amorphous areas were gone and the sample was now highly crystalline. A sample was withdrawn on a glass filter with porosity 4 and dried in vacuum at 22° C. and subsequently analysed. The DSC thermogram contained one endothermic peak at 95° C. (onset=86° C.) with an enthalpy of 64 J/g and the TGA weight loss below 105° C. was 7.1%. The lower enthalpy obtained in this Example compared to that in Example 1 above is a result of baseline effects.

EXAMPLE 5

Crystallisation of Compound A

Ca. 10 ml of amorphous Compound A in ethyl acetate was evaporated to a gel. To this was added 2 ml of isopropanol plus some seeds of Compound A (from Example 3), and the mixture was left to stir overnight in a closed vessel. The next morning it had crystallized as verified with polarized light microscopy (by visual inspection of crystals between crossed polarizers).

EXAMPLE 6

Larger Scale Crystallization of Compound A

1 L of amorphous Compound A in ethyl acetate was evaporated to a thick, yellowish gel. To this was added ca. 30 ml isopropanol and the sample was then stirred until it was dissolved. Stirring then continued in a closed vessel and one day later some precipitation was observed. Since the progress was slow some seeds of Compound A (from Example 5), were added and the sample was then left stirred also in a closed vessel. Three days later the mixture had crystallized into a thick solid lump. Ca 50 ml+50 ml of isopropanol were added so that the solid could be re-dispersed and filtered onto a glass-filter with porosity 3. The sample was then transferred from the filter to a large glass bowl in which it was dried in vacuum at 50° C. for 1 day (the material was taken out and lumps were occasionally crushed manually). The sample was crystalline and had an XRPD-diffractogram very similar to that in FIG. 1 (see Example 20). The DSC thermogram contained one endothermic peak at 112° C. (onset=106° C.) with a melting enthalpy of 89 J/g and the TGA weight loss below 120° C. was 0.1%.

EXAMPLE 7

Solubility of Compound A in Ethyl Acetate

An excess of Compound A from Example 3 above was slurried in ethyl acetate for one day. A proportion of the saturated solution was then withdrawn through a 0.5 micrometer filter to a pre-weighted E-flask. The E-flask was weighed and then opened & evaporated in air, and then dried in vacuum at 40° C. until the weight was constant. The weight of the solution, the weight of dry substance, the weight of solvent and the volume of solvent were determined (using the density of ethyl acetate at 22° C.=0.90 g/ml).

The solubility (as mg of Compound A per ml ethyl acetate)=36 mg/ml.

The solubility as weight %=4% w/w.

EXAMPLE 8

Solubility of Compound B in Isopropanol

An excess of Compound B from Example 2 above was slurried in isopropanol for one day in a closed vessel. A proportion of the saturated solution was then withdrawn through a 0.5 micrometer filter to a pre-weighted E-flask. The E-flask was weighed and then opened & evaporated in air, and then dried in vacuum at 70° C. until the weight was constant. The weight of the solution, the weight of dry substance, the weight of solvent and the volume of solvent were determined (using the density of isopropanol at 22° C.=0.79 g/ml).

The solubility (as mg of Compound B per ml isopropanol)=3 mg/ml.

The solubility as weight %=0.4% w/w.

EXAMPLE 9

Solubility of Compound A Anhydrate in Isopropanol

An excess of Compound A from Example 6 above was slurried in isopropanol for one day in a closed vessel. A proportion of the saturated solution was then withdrawn through a 0.5 micrometer filter to a pre-weighted E-flask. The E-flask was weighed and then opened & evaporated in air, and then dried in vacuum at 70° C. until the weight was constant. The weight of the solution, the weight of dry substance, the weight of solvent and the volume of solvent were determined (using the density of isopropanol at 22° C.=0.79 g/ml).

The solubility (as mg of Compound A per ml isopropanol)=15 mg/ml.

The solubility as weight %=2% w/w.

EXAMPLE 10

Crystallisation of Compound A in Isopropanol

Amorphous Compound A (100.1 mg) was weighed into a test tube and then a stirring magnet and 1.00 ml of isopropanol was added. The tube was capped with a tight sealing cap and then put on a magnetic stirrer at 22° C. The solid was dissolved after a few minutes stirring and the sample was then left stirring. After 17.5 hours the tube was inspected and it was found that a large amount of solid had precipitated. In order to become more fully precipitated the sample was stirred for 3 more days and then a slurry sample was withdrawn and dripped onto a Silicon zero background holder. The sample was left to dry and was then analysed with XRPD and gave a diffractogram similar to that in FIG. 1 (see Example 20), but with preferred orientation effects.

EXAMPLE 11

Crystallisation of Compound A in Isopropanol

Amorphous Compound A (80.1 mg) was weighted into a test tube and then a stirring magnet and 1.00 ml of isopropanol was added. The tube was capped with a tight sealing cap and was then put on a magnetic stirrer at 22° C. The solid was dissolved after a few minutes stirring and the sample was then left stirred. After 17.5 hours the tube was inspected and it was found that a large amount of solid had precipitated. In order to become more fully precipitated the sample was stirred for 3 more days and then a slurry sample was withdrawn and dripped onto a Silicon zero background holder. The sample was left to dry and was then analysed with XRPD and gave a diffractogram similar to that in FIG. 1 (see Example 20), but with preferred orientation effects.

EXAMPLE 12

Crystallisation of Compound A in Isopropanol

Amorphous Compound A (59.8 mg) was weighted into a test tube and then a stirring magnet and 1.00 ml of isopropanol was added. The tube was capped with a tight sealing cap and was then put on a magnetic stirrer at 22° C. The solid was dissolved after a few minutes stirring and the sample was then left stirred. After 17.5 hours the tube was inspected and it was found that a large amount of solid had precipitated. In order to become more fully precipitated the sample was stirred for 3 more days and then a slurry sample was withdrawn and dripped onto a Silicon zero background holder. The sample was left to dry and was then analysed with XRPD and gave a diffractogram similar to that in FIG. 1 (see Example 20), but with preferred orientation effects.

EXAMPLE 13

Crystallisation of Compound A in Isopropanol

Amorphous Compound A (40.9 mg) was weighted into a test tube and then a stirring magnet and 1.00 ml of isopropanol was added. The tube was capped with a tight sealing cap and was then put on a magnetic stirrer at 22° C. The solid was dissolved after a few minutes stirring and the sample was then left stirred. After 17.5 hours the tube inspected but no solid had precipitated. The sample was stirred for 3 more days and then a slight precipitation was noted. After 3 more days the sample contained a large amount of solid material. A slurry sample was now withdrawn and dripped onto a Silicon zero background holder. The sample was left to dry and was then analysed with XRPD and gave a diffractogram similar to that in FIG. 1 (see Example 20), but with preferred orientation effects.

EXAMPLE 14

Crystallisation of Compound A in Isopropanol

Amorphous Compound A (19.6 mg) was weighed into a test tube and then a stirring magnet and 1.00 ml of isopropanol was added. The tube was capped with a tight sealing cap and was then put on a magnetic stirrer at 22° C. The solid was dissolved after a few minutes stirring and the sample was then left stirred. As a result of the low supersaturation, after 1.5 months the sample was still not precipitated.

EXAMPLE 15

Additional Analyses of Samples from Experiments 10-13

After 7.5 days of stirring the samples in Examples 10 to 13 above were all collected into one sample on a filter with porosity 1.2 micrometers. The sample was dried for 1 hour in vacuum oven at 50° C. and was then smeared onto a Silicon zero background holder and analysed with XRPD. The X-Ray diffractogram was very similar to that in FIG. 1 (see Example 20). A portion of the dried sample was then analysed with TGA. It showed no significant weight losses below 200° C. The sample was then analysed with DSC using a 10° C./min scan and a melting endotherm with a corrected onset melting temperature of 109° C. was found.

EXAMPLE 16

Crystallisation of Compound A in Ethyl Acetate

Amorphous Compound A (160.5 mg) was weighed into a test tube and then a stirring magnet and 1.00 ml of ethyl acetate was added. The tube was capped with a tight sealing cap and was then put on a magnetic stirrer at 22° C. The solid was dissolved after a few minutes stirring and the sample was then left stirred. After 17.5 hours the tube was inspected and it was found that a slight amount of solid had precipitated. In order to become more fully precipitated the sample was stirred for 3 more days and then a slurry sample for XRPD was withdrawn and dripped onto a silicon zero background holder. After drying an XRPD analysis was performed, which gave a diffractogram similar to that in FIG. 1 (see Example 20), but with preferred orientation effects.

EXAMPLE 17

Crystallisation of Compound A in Ethyl Acetate

Amorphous Compound A (140.8 mg) was weighed into a test tube and then a stirring magnet and 1.00 ml of ethyl acetate was added. The tube was capped with a tight sealing cap and was then put on a magnetic stirrer at 22° C. The solid was dissolved after a few minutes stirring and the sample was then left stirred. After 17.5 hours the tube was inspected and it was found that a slight amount of solid had precipitated. In order to become more fully precipitated the sample was stirred for 3 more days and then a slurry sample for XRPD was withdrawn and dripped onto a silicon zero background holder. After drying an XRPD analysis was performed, which gave a diffractogram similar to that in FIG. 1 (see Example 20), but with preferred orientation effects.

EXAMPLE 18

Crystallisation of Compound A in Ethyl Acetate

Amorphous Compound A (120.3 mg) was weighed into a test tube and then a stirring magnet and 1.00 ml of ethyl acetate was added. The tube was capped with a tight sealing cap and was then put on a magnetic stirrer at 22° C. The solid was dissolved after a few minutes stirring and the sample was then left stirred. After 17.5 hours the tube was inspected and it was found that a slight amount of solid had precipitated. In order to become more fully precipitated the sample was stirred for 3 more days and then a slurry sample for XRPD was withdrawn and dripped onto a silicon zero background holder. After drying an XRPD analysis was performed, which gave a diffractogram similar to that in FIG. 1 (see Example 20), but with preferred orientation effects.

EXAMPLE 19

Crystallisation of Compound A in Ethyl Acetate

Amorphous Compound A (99.5 mg) was weighed into a test tube and then a stirring magnet and 1.00 ml of ethyl acetate was added. The tube was capped with a tight sealing cap and was then put on a magnetic stirrer at 22° C. The solid was dissolved after a few minutes stirring and the sample was then left stirred. After 17.5 hours the tube inspected but no solid had precipitated. The sample was stirred for 3 more days and then a slight precipitation was noted. After 3 more days the sample contained a large amount of solid material. A slurry sample was now withdrawn and dripped onto a Silicon zero background holder. The sample was left to dry and was then analysed with XRPD which gave a diffractogram similar to that in FIG. 1 (see Example 20), but with preferred orientation effects.

EXAMPLE 20

Crystallisation of Compound A in Ethyl Acetate

Figure 1:
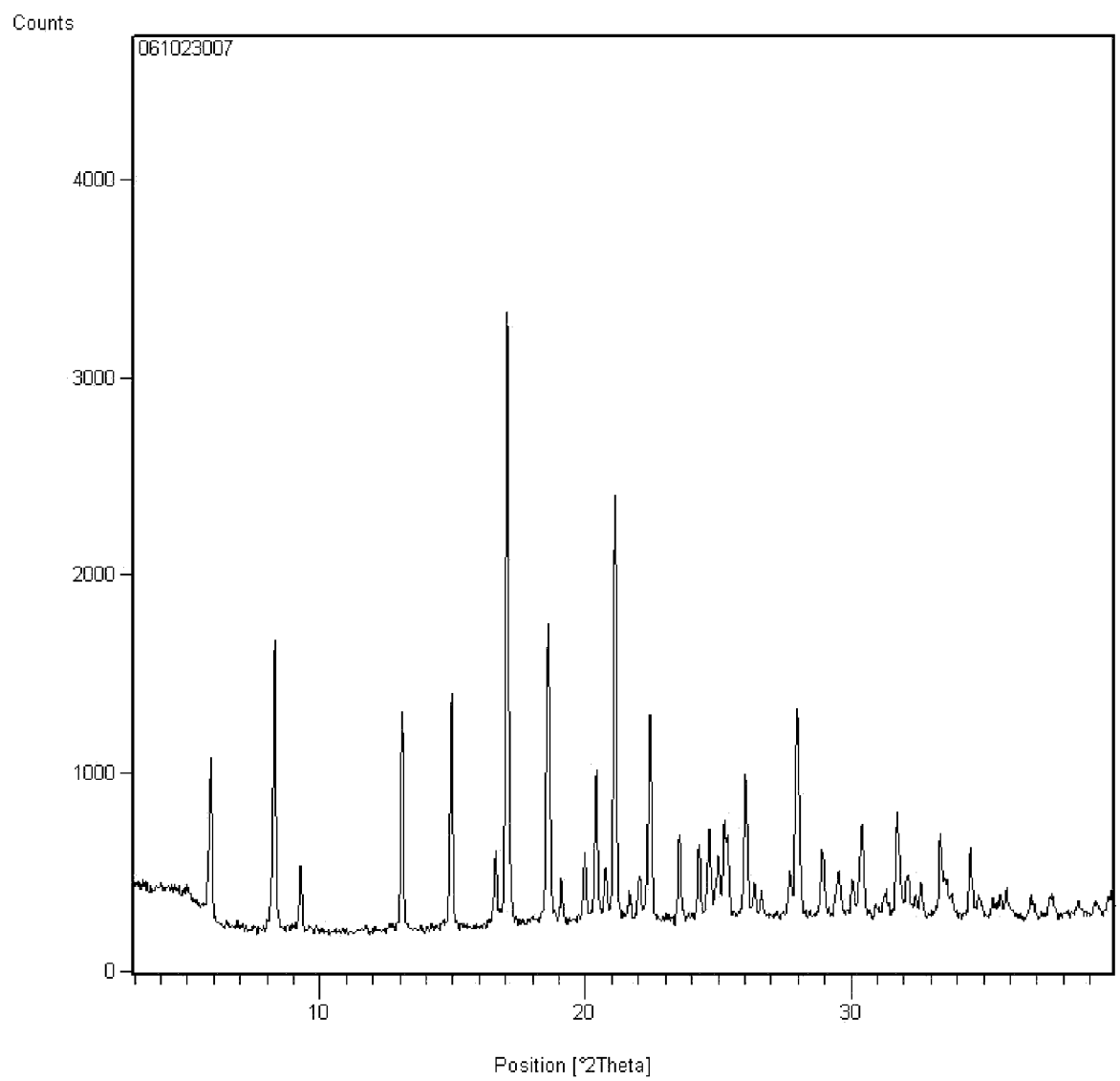
FIG. 1 shows the XRPD-diffractogram of crystalline anhydrate of Compound A.

Amorphous Compound A (80.4 mg) was weighed into a test tube and then a stirring magnet and 1.00 ml of ethyl acetate was added. The tube was capped with a tight sealing cap and was then put on a magnetic stirrer at 22° C. The solid was dissolved after a few minutes stirring and the sample was then left stirring. After 17.5 hours the tube inspected but no solid had precipitated. After 7.5 days a slight precipitation was beginning to appear. The amount was however too small for analysis. Some 40 days later the sample had precipitated more fully. The solid was collected on a filter with porosity 1.2 micrometers. The sample was dried for 1 hour in vacuum oven at 50° C. and was then smeared onto a Silicon zero background holder and analysed with XRPD. The X-Ray diffractogram obtained is shown in FIG. 1.

EXAMPLE 21

Analyses of Samples from Experiments 16-19

After 7.5 days of stirring the samples in Experiments 16 to 19 above were all collected into one sample on a filter with porosity 1.2 micrometers. The sample was dried for 1 hour in vacuum oven at 50° C. and was then smeared onto a Silicon zero background holder and analysed with XRPD. The X-Ray diffractogram was very similar to that in FIG. 1 (see Example 20). A portion of the dried sample was then analysed with TGA. It showed no significant weight losses below 200° C. The sample was then analysed with DSC using a 10° C./min scan and a melting endotherm with a corrected onset melting value of 109° C. was found.

EXAMPLE 22

Solubility of Compound A in Ethanol

An excess of Compound A from Example 6 above was slurried in ethanol for one day in a closed vessel. A proportion of the saturated solution was then withdrawn through a 0.5 micrometer filter to a pre-weighed E-flask. The E-flask was weighed and then opened and evaporated in air, and then dried in vacuum at 40-50° C. until the weight was constant. The weight of the solution, the weight of dry substance, the weight of solvent and the volume of solvent were determined (using the density of ethanol at 22° C.=0.79 g/ml).

The solubility (as mg of Compound A per ml ethanol)=87 mg/ml.

The solubility as weight %=10% w/w.

EXAMPLE 23

Solubility of Compound A in Methanol

An excess of Compound A from Example 6 above was slurried in methanol for one day in a closed vessel. A proportion of the saturated solution was then withdrawn through a 0.5 micrometer filter to a pre-weighted E-flask. The E-flask was weighed and then opened & evaporated in air, and then dried in vacuum at 40-50° C. until the weight was constant. The weight of the solution, the weight of dry substance, the weight of solvent and the volume of solvent were determined (using the density of methanol at 22° C.=0.79 g/ml).

The solubility (as mg of Compound A per ml methanol)=655 mg/ml.

The solubility as weight %=45% w/w.

EXAMPLE 24

Solubility of Compound A in Acetone

An excess of Compound A from Example 6 above was slurried in acetone for one day in a closed vessel. A proportion of the saturated solution was then withdrawn through a 0.5 micrometer filter to a pre-weighted E-flask. The E-flask was weighed and then opened & evaporated in air, and then dried in vacuum at 70° C. until the weight was constant. The weight of the solution, the weight of dry substance, the weight of solvent and the volume of solvent were determined (using the density of acetone at 22° C.=0.82 g/ml).

The solubility (as mg of Compound A per ml acetone)=398 mg/ml.

The solubility as weight %=33% w/w.

EXAMPLE 25

Pellet Formulation with Enteric Coating

Compound A crystalline anhydrate (223 g) was suspended in 750 g of a 2.5% (w/w) HPMC (6 cps)/water solution by mixing in a Silverson blender for more than 4 hours.

Micro-crystalline cellulose (MCC) cores (170 g; Celphere 305, Asahi Casei) were used as starting material and spray layering was carried out in a Wurster fluid bed equipment yielding 370 g of pellets.

Ethyl cellulose (16.7 g) and hydroxypropyl cellulose (15.6 g) were dissolved in 450 g of 99.5% EtOH.

360 g of the pellets were then coated with the EC/HPC/EtOH solution yielding 389 g of coated pellets.

These pellets (350 g) were finally coated with an Eudragit L30D (Degussa) aqueous dispersion corresponding to 56 g of dry material and yielding 401 g of enteric coated pellets.

The release profile of the pellet formulation was studied using standard techniques (LC was used to determine material released) at pH 1 (0.1M HCl) and pH 6.8 (phosphate buffer). The results show that at pH 1 there is virtually no active ingredient material released (approximately 1-2%) from the formulation over 24 hours. However, at pH 6.8 approximately 21% of active material is released over 3 hours; 39% over 6 hours; 49% over 8 hours; 79% over 16 hours; 88% over 20 hours and 99% over 32 hours.

EXAMPLE 26

Gelling Matrix Formulation

Preparation of Granulating Solution

The granulating liquid was prepared by dissolving hydroxypropyl cellulose in ethanol while stirring.

Granulation

Hydroxypropyl methylcellulose and Compound A crystalline anhydrate were then mixed in a Mini Diosna mixer with a 1 L vessel. While mixing, the granulating fluid was added over 4-6 minutes. If necessary more ethanol is added.

Drying and Milling

The wet mass was dried in a hot air oven and the dried mass milled using a Quadro Comill 1.57 mm mesh.

Final Mixing and Tableting

The granulate was then mixed with 2% sodium stearyl fumarate in a Turbula blender. The granulate was compressed in an Excenterpress using 9 mm punches. Tablet weight 273 mg, tablet hardness >60 N.

Final Composition

| Component | mg/tablet | % |
|---|---|---|
| Compound A crystalline anhydrate | 150 | 55 |
| Hydroxypropyl metylcellulose 50 mPas | 109 | 40 |
| Hydroxypropylcellulose LF | 8.2 | 3 |
| Sodium stearyl fumarate | 5.5 | 2 |
| Ethanol 99.5% (evaporates during processing) | q.s. | — |

The release profile of 150 mg and 200 mg gelling matrix formulations was studied using standard techniques (LC was used to determine material released) at pH 1 (0.1M HCl) and pH 6.8 (phosphate buffer). The results are illustrated in FIG. 4 for Example 26.

EXAMPLE 27

Crystallization of Compound A in Isopropyl Acetate/Ethanol/Heptane

An isopropyl acetate solution (165.27 g) containing Compound A (40 g) was filtered through a ceramic glass filter at ambient temperature. The filter was rinsed with 36 mL ethanol and the two solutions poured together into a 0.5 L reactor equipped with a mechanical impeller and heated to 30° C. After about 20 minutes, seeds of crystalline Compound A anhydrate (4% w/w, based on 100% product) were added to the stirred solution to initiate crystallization. After an additional 15 minutes, 120 mL heptane was added over 2 hrs. The slurry was stirred for about 14 hrs. at 30° C. and then a second addition of heptane (160 mL) was performed over 2 hrs. The slurry was cooled to 20° C. during this addition (2 hrs. cooling time). After an additional 10 hrs. the solid substance was isolated by filtration. The filter cake was washed twice with mixtures of 25 mL isopropyl acetate, 6 mL ethanol and 49 mL heptane. Finally it was dried overnight under vacuum at 40° C. (yield 38.2 g). XRPD corresponded to the reference of anhydrate Compound A disclosed herein.

The seed crystals used above were obtained from similar earlier experiments using a lower quantity of Compound A seeds (such seeds being obtained from an earlier similar experiment performed over a longer time). Compound A seeds for earlier similar experiments are obtained from similar experiments including those described herein.

The invention claimed is:

1. The compound Ph(3-Cl)(5-OCHF$_2$)—(R)CH(OH)C(O)-Aze-Pab(OMe) in a substantially crystalline anhydrate form having an X-ray powder diffraction pattern characterized by peaks with d-values at 5.2 Å, 4.79 Å, 4.23 Å and 3.98 Å.

2. The compound as claimed in claim 1 having an X-ray powder diffraction pattern characterized by peaks with d-values at 15.2 Å, 10.8 Å, 6.8 Å, 6.0 Å, 5.2 Å, 4.79 Å, 4.23 Å and 3.98 Å.

3. The compound as claimed in claim 2, characterised by a differential scanning calorimetry curve, at a heating rate of 10° C./min in a closed cup with pinholes under flowing nitrogen, exhibiting an endotherm with an extrapolated onset temperature of about 109° C. and a peak temperature of about 115° C.

4. The compound as claimed in claim 1 having an X-ray powder diffraction pattern substantially as shown in FIG. 1.

5. The compound as claimed in claim 1 wherein the crystallinity is greater than 80%.

* * * * *